(12) United States Patent
Kumar et al.

(10) Patent No.: US 7,875,426 B2
(45) Date of Patent: Jan. 25, 2011

(54) DNA BIOCHIP AND METHODS OF USE

(75) Inventors: Arun Kumar, Tampa, FL (US); Ashok Kumar, Tampa, FL (US); Shree R. Singh, Montgomery, AL (US); Souheil Zekri, Tampa, FL (US)

(73) Assignees: University of South Florida, Tampa, FL (US); Alabama State University, Montgomery, AL (US)

( * ) Notice: Subject to any disclaimer, the term of this patent is extended or adjusted under 35 U.S.C. 154(b) by 285 days.

(21) Appl. No.: 11/347,438

(22) Filed: Feb. 3, 2006

(65) Prior Publication Data

US 2007/0015175 A1 Jan. 18, 2007

Related U.S. Application Data

(60) Provisional application No. 60/649,961, filed on Feb. 4, 2005.

(51) Int. Cl.
*C12Q 1/68* (2006.01)
*C12M 1/36* (2006.01)
*C07H 21/04* (2006.01)
*G01N 15/06* (2006.01)

(52) U.S. Cl. ................ 435/6; 435/283.1; 435/287.2; 422/68.1; 422/82.01; 536/23.1

(58) Field of Classification Search ................ None
See application file for complete search history.

(56) References Cited

U.S. PATENT DOCUMENTS 5,206,149 A * 4/1993 Oyama et al. ............ 435/28
5,223,254 A * 6/1993 Paradiso et al. .......... 424/186.1
5,688,642 A * 11/1997 Chrisey et al. ............ 435/6
6,017,696 A * 1/2000 Heller ...................... 435/6

(Continued)

FOREIGN PATENT DOCUMENTS

WO  WO 01/01139  * 1/2001

OTHER PUBLICATIONS

Li et al "Optical DNA biosensor based on molecular beacon immobilized on Sol-Gel membrane" Proceedings of SPIE, 2001, vol. 4414: 27-30.*

(Continued)

*Primary Examiner*—BJ Forman
(74) *Attorney, Agent, or Firm*—Saliwanchik, Lloyd & Saliwanchik

(57) ABSTRACT

The subject invention concerns materials and methods for detecting nucleic acid sequences. One aspect of the invention concerns a silicon-based "biochip" comprising nucleic acid immobilized thereon. In one embodiment, the silicon comprises microcavities. The nucleic acid to be assayed for the presence of one or more target nucleic acid sequences is immobilized on the silicon. A nucleic acid, such as an oligonucleotide probe, having a sequence substantially complementary to the target nucleic acid sequence can be used to detect the immobilized nucleic acid on the silicon. If the nucleic acid used for detection hybridizes with a target nucleic acid sequence, the hybridized sequences can be detected directly or indirectly. In an exemplified embodiment, the oligonucleotide probe can be labeled with a detectable label, for example, a fluorescent molecule. The subject invention also concerns methods for detecting a target nucleic acid using a silicon-based biochip of the invention.

34 Claims, 9 Drawing Sheets
(6 of 9 Drawing Sheet(s) Filed in Color)

U.S. PATENT DOCUMENTS

| | | | | |
|---|---|---|---|---|
| 6,066,448 | A | * | 5/2000 | Wohlstadter et al. ............ 435/6 |
| 6,117,643 | A | * | 9/2000 | Simpson et al. .............. 435/7.1 |
| 6,303,290 | B1 | | 10/2001 | Liu et al. |
| 6,495,352 | B1 | | 12/2002 | Brinker et al. |
| 6,730,212 | B1 | * | 5/2004 | Yamagishi et al. ....... 205/777.5 |
| 2003/0148291 | A1 | * | 8/2003 | Robotti .......................... 435/6 |
| 2006/0068407 | A1 | * | 3/2006 | Rupcich et al. ................ 435/6 |

OTHER PUBLICATIONS

Anselmetti, D. et al. "Single Molecule DNA Biophysics with Atomic Force Microscopy," *Single Mol.*, (2000), pp. 53-58, vol. 1, No. 1.

Brinker, C.J. et al. "Sol→Gel→Glass :I. Gelation and Gel Structure," *J. Non-Crystalline Solids*, (1985), pp. 301-322, vol. 70.

Broude, N. E. "Stem loop oligonucleotides:a robust tool for molecular biology and biotechnology," *TRENDS in Biotechnology*, (2002), pp. 249-256, vol. 20, No. 6.

Canham, L.T. "Silicon quantum wire array fabrication by electrochemical and chemical dissolution of wafers," *Appl. Phy Lett.*, (Sep. 3, 1990), pp. 1046-1048, vol. 57, No. 10.

Chan, S. et al. "Porous Silicon Microcavities for Biosensing Applications," *Phys. Stat. Sol. A*, (2000), pp. 541-546, vol. 182.

Cluzel, P. et al. "DNA: An Extensible Molecule," *Science*, (Feb. 9, 1996), pp. 792-794, vol. 271.

Drobyshev, A. et al. "Sequence analysis by hybridization with oligonucleotide microchip: identification of β-thalassemia mutations," *Gene*, (1997), pp. 45-52, vol. 188.

Fink, H.W. et al. "Electrical conduction through DNA molecules," *Science*, (Apr. 1, 1999), pp. 407-410, vol. 398.

Garcia-Parajó, M.F. et al. "Optical Probing of Single Fluorescent Molecules and Proteins," *Chem Phys Chem*, (2001), pp. 347-360, vol. 2, No. 6.

Goryachev, D. N. et al. "Electrolytic Fabrication of Porous Silicon with the Use of Internal Current Source," *Semiconductors*, (2003), pp. 477-481, vol. 37, No. 4.

Guckenberger, R. et al. "Scanning Tunneling Microscopy of Insulators and Biological Specimens Based on Lateral Conductivity of Ultrathin Water Films," *Science*, (Dec. 2, 1994), pp. 1538-1540, vol. 266.

Hansma, H.G. et al. "Atomic force microscopy of single- and double-stranded DNA," *Nucleic Acids Res.*, (1992), pp. 3585-3590, vol. 20, No. 14.

Hench, L.L. et al. "The Sol-Gel Process," *Chem. Rev.*, (1990), pp. 33-72, vol. 90.

Isola, N.R. et al. "Surface-Enhanced Raman Gene Probe for HIV Detection," *Anal. Chem.*, (1998), pp. 1352-1356, vol. 70.

Lauerhaas, J.M. et al. "Chemical Modification of the Photoluminescence Quenching of Porous Silicon," *Science*, (Sep. 17, 1993), pp. 1567-1568, vol. 261.

Janshoff, A. et al. "Macroporous p-Type Silicon Fabry-Perot Layers. Fabrication, Characterization, and Application in Biosensing," *J. Amer. Chem. Soc.*, (1998), pp. 12108-12116, vol. 120.

Kumar, A. et al. "Co-immobilization of cholesterol oxidase and horseradish peroxidase in a sol-gel film," *Analytica Chimica Acta*, (2000), pp. 43-50, vol. 414, Nos. (1-2).

Meurman, O. et al. "Diagnosis of Respiratory Syncytial Virus Infection in Children: Comparison of Viral Antigen Detection and Serology," *J. Med. Virol.*, (1984a), pp. 61-65, vol. 14.

Meurman, O. et al. "Immunoglobulin Class-Specific Antibody Response in Respiratory Syncytial Virus Infectioin Measured by Enzyme Immunoassay," *J Med. Virol.*, (1984b), pp. 67-72, vol. 14.

Mirzabekov, A.D. "DNA sequencing by hybridization a mega sequencing method and a diagnostic tool" *TIBTECH*, (Jan. 1994), pp. 27-32, vol. 12.

Richardson, L.S. et al. "Enzyme-Linked Immunosorbent Assay for Measurement of Serological Response to Respiratory Syncytial Virus Infection," *Infect. Immun.*, (1978), pp. 660-664, vol. 20, No. 3.

Selvin, P.R. "The renaissance of fluorescence resonance energy transfer," *Nat. Struct. Biol.*, (Sep. 2000), pp. 730-734, vol. 7, No. 9.

Singh, Y. et al. "Fluorescence Resonance Energy Transfer: A Diagnostic Tool in Oligonucleotide Therapy," *Curr. Sci.*, (2000), pp. 487-492, vol. 78.

Smith, S.B. et al. "Direct Mechanical Measurements of the Elasticity of Single DNA Molecules by Using Magnetic Beads," *Science*, (Nov. 13, 1992), pp. 1122-1126, vol. 258.

Smith, R.L. et al. "Porous silicon formation mechanisms," *J. Appl. Phy.*, (Apr. 15, 1992), pp. 1-22, vol. 71, No. 8.

Smith, S.B. et al. "Overstretching B-DNA: The Elastic Response of Individual Double-Stranded and Single-Stranded DNA Molecules," *Science*, (Feb. 9, 1996), pp. 795-799, vol. 271.

Speel, E.J.M. et al. Amplification Methods to Increase the Sensitivity of In Situ Hybridization: Play CARD(S), *The Journal of Histochemistry & Cytochemistry*, (1999), pp. 281-288, vol. 47, No. 3.

Strick, T.R. et al., "The Elasticity of a Single Supercoiled DNA Molecule," *Science*, (Mar. 29, 1996), pp. 1835-1837, vol. 271.

Uhlir, A. "Electrolytic Shaping of Germanium and Silicon," *Bell Syst. Tech. J.*, (Mar. 1956), pp. 333-347, vol. 35.

Welliver, R.C. et al. "The anitbody response to primary and secondary infection with respiratory syncytial virus: Kinetics of class-specific responses," *J. Pediatr.*, (May 1980), pp. 808-813, vol. 96.

Wang, M.D. et al. "Stretching DNA with Optical Tweezers," *Biophys. J.*, (Mar. 1997), pp. 1335-1346, vol. 72.

Wennmalm, S. et al. "Conformational fluctuations in single DNA molecules," *Proc. Natl. Acad. Sci.*, (Sep. 1997), pp. 10641-10646, vol. 94.

Wittwer, C.T. et al. "Continuous Fluorescence Monitoring of Rapid Cycle DNA Amplification," *Biotechniques*, (1997), pp. 130-138, vol. 22, No. 1.

Yanagida, M. et al. *Cold Spring Harbor Symp. Quant .Biol.*, (1983), p. 177, vol. 47.

Yang, T. T. et al. "Optimized Codon Usage and Chromophore Mutations Provide Enhanced Sensitivity with the Green Fluorescent Protein," *Nucleic Acid Research*, (1996), pp. 4592-4593, vol. 24, No. 22. Genbank accession No. NC 001781.

Kumar A. et al. "Nanoscale Silicon Microcavity DNA Biosensor" *Poster Presentation at 1st International Conference of Nanotechnology* (Nanotech), Jul. 2004.

Karron, R.A., et al. "Respiratory syncytial virus (RSV) SH and G proteins are not essential for viral replication in vitro: Clinical evaluation and molecular characterization of a cold-passaged, attenuated RSV subgroup B mutant" *Proc. Natl. Acad. Sci. U.S.A.*, (1997), pp. 13961-13966, vol. 94, No. 25.

\* cited by examiner

DNA BIOCHIP AND METHODS OF USE

CROSS-REFERENCE TO A RELATED APPLICATION

This application claims the benefit of U.S. Provisional Application Ser. No. 60/649,961, filed Feb. 4, 2005, which is hereby incorporated by reference herein in its entirety, including any figures, tables and drawings.

BACKGROUND OF THE INVENTION

DNA plays an important role in many cellular processes like replication, homologous recombination and transcription. Besides its genomic information, DNA exhibits very interesting biophysical and physicochemical properties which are essential for proper functioning of the biomolecular processes involved. Biochips, particularly those based on DNA are powerful devices that integrate the specificity and selectivity of biological molecules with electronic control and parallel processing of information. This combination will potentially increase the speed and reliability of biological analysis. Microelectronic technology is especially suited for this purpose since it enables low-temperature processing and thus allows fabrication of electronics devices on a wide variety of substances like glass, plastic, stainless steel and silica wafer. Fundamental phenomena like molecular elasticity, binding to protein, supercoilling and electronic conductivity also depends on the numerous possible DNA confirmations and can be investigated nowadays on a single molecule level. Experiments with single DNA have been reported with scanning tunneling microscopy (Guckenberger et al., 1994), fluorescence microscopy (Yanagida et al., 1983), fluorescence correlation spectroscopy (Wannmalm et al., 1997), optical tweezers (Smith et al., 1996), bead techniques in magnetic fields (Wang et al., 1997), optical microfibers (Strick et al., 1996), electron holography (Smith et al., 1992a) and atomic force microscopy (Cluzel et al., 1996; Fink et al., 1999; Hansma et al., 1991). All these methods provide, directly or indirectly, information on molecular structure and function. They differ, however, in the molecular properties they probe, their spatial and temporal resolution, their molecular sensitivity and working environment.

Fluorescently labeled oligonucleotide probes are in regular use for nucleic acid sequencing (Mirzabekov, 1994), sequencing by hybridization (SBH) (Speel et al., 1999), fluorescence in situ hybridization (FISH) (Lakowicz et al., 1999), fluorescence resonance energy transfer (FRET) (Selvein, 2000), molecular beacons (Singh et al., 2000), taqman probes (Broude, 2002), and chip-based DNA arrays (Wittwer et al., 1997). This has made fluorescent probes an important tool for clinical diagnostics and made possible real-time monitoring of oligonucleotide hybridization. Furthermore, fluorescent-based diagnostics avoid the problem of storage, stability, and disposal of radioactive labels (Schena, 2000; Drobyshov et al., 1997).

Knowledge of structural and physical properties in microbial cells and microbial cell components is required to obtain a comprehensive understanding of cellular process and their dynamics. The need for a nondestructive method was satisfied with the development of the Atomic Force Microscope (AFM). The last 15 years have witnessed the extraordinary growth of structural studies in biology, and the impact is being felt in almost all areas of biological research. Several groups have used microscopy for the analysis of DNA, protein, and DNA-protein interactions. Until recently, electron microscopy was used as the main tool for imaging DNA; however this technique can be harsh on biological samples, making successful analysis extremely difficult. Approximately a decade ago, scientists began to use AFM for the analysis of biological samples. AFM allowed the analysis of biological molecules to be performed faster, easier and more accurately yielding successful characterization of biological specimens. The development of the AFM and its introduction for imaging biological samples has provided scientists with a very powerful tool to explore many aspects of protein-protein, protein-DNA and many other interactions (Fritz et al., 2000).

Various methods can be employed to bind DNA to different hosts. An array of substances, including catalytic antibodies, DNA, RNA, antigens, live bacterial, fungal, plant and animal cells, and whole protozoa, have been encapsulated in silica, organosiloxane and hybrid sol-gel materials. Sol-gel immobilization leads to the formation of advanced materials that retain highly specific and efficient functionality of the guest biomolecules within the stable host sol-gel matrix (Hench et al., 1990). The protective action of the sol-gel cage prevents leaching and significantly enhances stability of biomolecules within the sol-gel. The advantages of these 'living ceramics' might give them applications as optical and electrochemical sensors, diagnostic devices, catalysts, and even bio-artificial organs. With rapid advances in sol-gel precursors, nanoengineered polymers, encapsulation protocols and fabrication methods, this technology promises to revolutionize bioimmobilization. Biosensors using immobilized receptors are finding ever-increasing application in a wide variety of fields such as clinical diagnostics, environmental monitoring, food and drinking water safety, and monitoring of illicit drugs (Brinker et al., 1985). One of the most challenging aspects in development of these sensors is immobilization and integration of biological molecules in the sensor platform. Numerous techniques, including physical covalent attachment, and entrapment in polymer and inorganic matrices, have been explored over the past decade. Sol-gel processes are promising host matrices for encapsulation of biomolecules such as enzymes, antibodies, and cells (Kumar et al., 2000).

Porous silicon (PS) was discovered in 1956 by Uhlir (Uhlir, 1956) while performing electropolishing experiments on Silicon wafers using a hydrofluoric acid (HF)-containing electrolyte. Uhlir found that by increasing the current over a certain threshold, a partial dissolution of the silicon wafer started to occur. Porous Silicon formation can be obtained by electrochemical dissolution of Silicon wafers in aqueous or ethanoic HF solutions.

Microcavities are of interest for a wide range of fundamental and applied studies, including investigations of cavity quantum electrodynamics (Smith et al., 1992b), optical elements for telecommunications (Goryachev et al., 2003), single-photon sources (Chan et al., 2000), and chemical or biological sensors (Isola et al., 1998). Microfabrication techniques allow reproducible fabrication of resonators with lithographically controlled dimensions. Using a combination of lithography and etching, semiconductor microcavities have been obtained.

Almost all children under two years of age are infected by RSV. Children with weaker immune systems are at greater risk. For better health of all infants, infants with symptoms of common cold, wheezing, pneumonia and bronchiolitis need to be diagnosed for the RSV infection. All hospitals and physicians providing pediatric health care need RSV diagnosis kits. Current methods of detection are based on one single technology, i.e., immunological assays and they are very expensive and have low sensitivity and specificity. A new more robust technology is needed to diagnose children infected with RSV with higher sensitivity and specificity and at a very lower cost.

BRIEF SUMMARY OF THE INVENTION

The subject invention concerns materials and methods for detecting a target nucleic acid comprising a nucleotide sequence of interest. One aspect of the invention concerns a silicon-based "biochip" comprising nucleic acid immobilized thereon. In one embodiment, the silicon-based biochip comprises microcavities. The nucleic acid to be assayed for the presence of one or more target nucleic acid sequences is immobilized on the silicon. In one embodiment, the nucleic acid is provided in a sol-gel composition. The nucleic acid can be immobilized in single stranded form. A detector nucleic acid, such as an oligonucleotide probe, having a sequence substantially complementary to the target nucleic acid sequence can be used to detect the immobilized nucleic acid on the silicon. If the nucleic acid used for detection hybridizes with a nucleotide sequence of a nucleic acid immobilized on the silicon, the hybridized sequences can be detected by direct or indirect means and thus the target nucleic acid is thereby detected. In an exemplified embodiment, the oligonucleotide probe can be labeled with a detectable label, for example, a fluorescent molecule.

The subject invention also concerns methods for detecting a target nucleic acid using a silicon-based biochip of the invention. In one embodiment, a sample to be tested for the presence of a target nucleic acid is contacted with a silicon biochip of the invention such that nucleic acid in the sample is immobilized on the silicon biochip. Preferably, the silicon is prepared so as to have microcavities. The nucleic acid to be assayed for the presence of one or more target nucleic acid sequences can be provided on the silicon surface in a sol-gel. The silicon biochip is then contacted with a detector nucleic acid that comprises a nucleotide sequence that is substantially complementary with the sequence of the target nucleic acid of interest under conditions that permit hybridization of the detector nucleic acid to the target nucleic acid. In one embodiment, the detector nucleic acid is labeled with a detectable moiety, such as a fluorescent molecule. Hybridization of the detector nucleic acid is indicative of the presence of the target nucleic acid. The present methods can be used to detect nucleic acid sequences associated with bacteria, viruses, fungi, protozoans, and the like. In an exemplified embodiment, the target nucleic acid sequence is from Respiratory Syncytial Virus (RSV).

BRIEF DESCRIPTION OF THE FIGURES

The file of this patent contains at least one drawing executed in color. Copies of this patent with the color drawings will be provided by the Patent and Trademark Office upon request and payment of the necessary fee.

FIG. 4A (10×), FIG. 4B (40×) and FIG. 4C (100×).

FIG. 5A (10×), FIG. 5B (40×) and FIG. 5C (100×).

FIG. 6A (10×), FIG. 6B (40×) and FIG. 6C (100×).

BRIEF DESCRIPTION OF THE SEQUENCES

Figure 1:
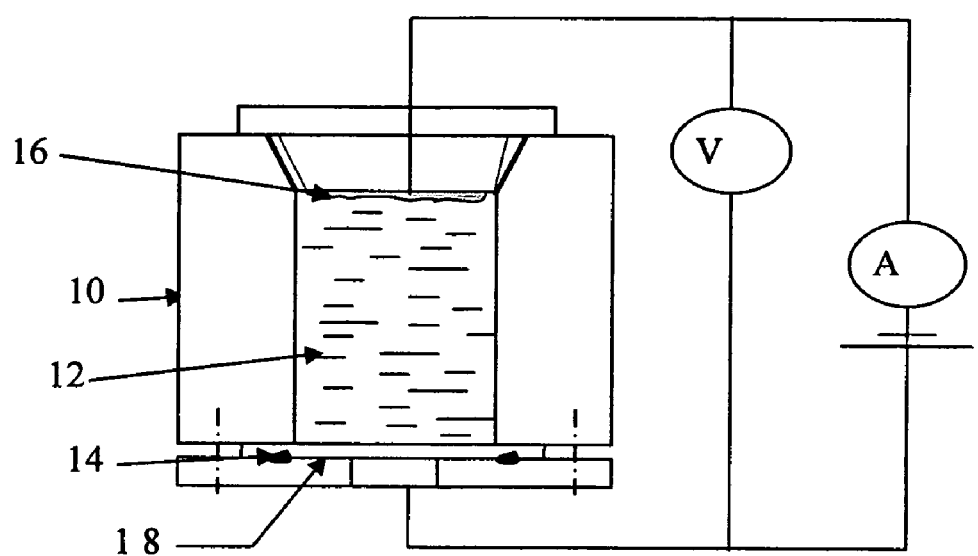
FIG. 1 shows the schematics of electrochemical etching of a silicon wafer.

SEQ ID NO: 1 is an oligonucleotide sequence corresponding to a sequence in the genome of Respiratory Syncytial Virus (RSV) F that is used in an exemplified embodiment of the present invention.

SEQ ID NO: 2 is an oligonucleotide sequence that is complementary to the sequence of SEQ ID NO: 1 and that is used in an exemplified embodiment of the present invention.

SEQ ID NO: 3 is the genomic nucleotide sequence for a Respiratory Syncytial Virus.

DETAILED DESCRIPTION OF THE INVENTION

The subject invention concerns materials and methods for detecting a target nucleic acid. One aspect of the invention concerns a silicon-based "biochip" comprising nucleic acid immobilized thereon. In one embodiment, the silicon comprises microcavities. Nucleic acid that is to be assayed for the presence of one or more target nucleic acid sequences is immobilized on the silicon. In one embodiment, the nucleic acid is immobilized in single stranded form. In a further embodiment, the nucleic acid is immobilized on the silicon using a sol-gel composition.

Sol-gel compositions and methods for incorporating a biomolecule, such as a nucleic acid, in sol-gel compositions are known in the art and have been described in U.S. Pat. Nos. 6,495,352 and 6,303,290, and in Kumar et al. (2000). A nucleic acid, such as an oligonucleotide probe, having a nucleotide sequence substantially complementary to a target nucleic acid sequence can be used to detect the immobilized nucleic acid on the silicon. If the nucleic acid used for detection hybridizes with a target nucleic acid sequence, the hybridized sequences can be detected either by direct or indirect means. In an exemplified embodiment, a nucleic acid (e.g., an oligonucleotide probe) can be labeled with a detectable label, for example, a fluorescent molecule.

The subject invention also concerns methods for detecting a target nucleic acid using a silicon-based biochip of the invention. In one embodiment, a sample to be tested for the presence of a target nucleic acid is contacted with the surface of a silicon biochip of the present invention such that nucleic acid present in the sample binds to and becomes immobilized on the silicon. Preferably, the silicon is prepared so as to have microcavities. The nucleic acid containing sample to be assayed for the presence of one or more target nucleic acid sequences can be provided on the silicon surface in a sol-gel composition. Optionally, the biochip can be washed to remove unbound nucleic acid. The silicon biochip is then contacted with a detector nucleic acid that comprises a nucleotide sequence that is substantially complementary with the sequence of the target nucleic acid of interest under conditions that permit hybridization of the detector nucleic acid to the target nucleic acid but that exclude non-specific binding of nucleic acid (i.e., conditions are such that nucleic acid that does not have a nucleotide sequence substantially complementary with the sequence of a target nucleic acid does not bind to the target nucleic acid or to the surface of the silicon). Optionally, the biochip can be washed to remove unbound detector nucleic acid. The hybridized nucleic acid is then detected by any suitable detection means. For example, if the detector nucleic acid is labeled with a fluorescent molecule, the fluorescence can be detected.

In a further embodiment, a nucleic acid complementary for a target nucleotide sequence is contacted with a surface of a silicon biochip of the present invention such that the nucleic acid binds to and becomes immobilized on the silicon. The silicon layer can be prepared so as to have microcavities. The nucleic acid containing sample to be assayed for the presence of one or more target nucleic acid sequences can be provided on the silicon surface in a sol-gel composition. Optionally, the biochip can be washed to remove unbound nucleic acid. The silicon biochip is then contacted with a nucleic acid containing sample to be screened for the presence of the target nucleotide sequence under conditions that permit hybridization of nucleic acids comprising the target nucleotide sequence with the immobilized nucleic acid but that exclude non-specific binding of nucleic acid. Optionally, the biochip can be washed to remove unbound nucleic acid. The hybridized nucleic acid is then detected by any suitable detection means.

In one embodiment, hybridization of nucleic acids is carried out under stringent hybridization conditions. As used herein, "stringent" conditions for hybridization refers to conditions wherein hybridization is typically carried out at about 12 to 25 degrees Celsius (C) below the effective melting temperature (Tm) of the DNA hybrid. The melting temperature, Tm, is described by the following formula (Beltz et al., 1983):

$$Tm=81.5\,C+16.6\,\text{Log}[Na+]+0.41(\%G+C)-0.61(\%\,\text{formamide})-600/\text{length of duplex in base pairs}.$$

Washes can be carried out as follows:

(1) Once or twice at room temperature for 15 minutes in 1×SSPE, 0.1% SDS (low stringency wash); and/or (2) Once at Tm-20 C for 15 minutes in 0.2×SSPE, 0.1% SDS (moderate stringency wash).

In one embodiment, a nucleic acid, for example, the detector nucleic acid, is labeled with a detectable moiety, such as a fluorescent molecule. Examples of detectable moieties include, but are not limited to, various enzymes, prosthetic groups, fluorescent materials, luminescent materials, bioluminescent materials, and radioactive materials. The detectable substance may be coupled or conjugated either directly to the nucleic acid or indirectly, though an intermediate (such as, for example, a linker known in the art) using techniques known in the art. Examples of suitable enzymes include, but are not limited to, horseradish peroxidase, alkaline phosphatase, beta-galactosidase, or acetylcholinesterase. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, Cascade Blue, rhodamine, dichlorotriazinylamine fluorescein, dansyl chloride, Texas Red, Oregon Green, cyanine (e.g., CY2, CY3, and CY5), allophycocyanine or phycoerythrin. An example of a luminescent material includes luminol. Examples of bioluminescent materials include, but are not limited to, luciferase, luciferin, green fluorescent protein (GFP), enhanced GFP (Yang et al., 1996), and aequorin. Hybridization of the detector nucleic acid is indicative of the presence of the target nucleic acid. In one embodiment, hybridization of the detector nucleic acid to the target nucleic acid is detected using atomic force microscopy (AFM). In another embodiment, hybridization of the detector nucleic acid to the target nucleic acid is detected by detecting the presence of the detectable moiety attached to the detector nucleic acid. In an exemplified embodiment, the detectable moiety is a fluorescent molecule.

In another embodiment, the detector nucleic acid is labeled with a first moiety that can bind to or be bound by a second moiety. In one embodiment, the first moiety is digoxigenin. The digoxigenin molecule can be incorporated into the nucleic acid molecule using digoxigenin conjugated nucleotides (e.g., digoxigenin-dUTP). The digoxigenin molecule can be detected using an antibody that binds to digoxigenin wherein the antibody has a detectable moiety, such as a fluorescent molecule, attached thereto. Alternatively, the antibody bound to digoxigenin can be detected by a second antibody that binds to the antidigoxigenin antibody wherein the second antibody has a detectable moiety, such as a fluorescent molecule, attached thereto. In another embodiment, a biotin-avidin or biotin-streptavidin system can be used. Thus, for example, the nucleic acid can have one or more biotin conjugated nucleotides (e.g., biotin-dUTP) incorporated into it. The biotin moiety can be detected using avidin, streptavidin, or other biotin-binding molecules that have a detectable moiety, such as a fluorescent molecule, attached thereto. Fluorescent molecules contemplated within the scope of the invention include, but are not limited to, umbelliferone, fluorescein, fluorescein isothiocyanate, Cascade Blue, rhodamine, dichlorotriazinylamine fluorescein, dansyl chloride, Texas Red, Oregon Green, cyanine (e.g., CY2, CY3, and CY5), allophycocyanine or phycoerythrin.

The present methods can be used to detect nucleic acid sequences associated with animals, including mammals (e.g., humans), plants, bacteria, viruses, fungi, protozoans, and the like. In one embodiment, the target nucleic acid sequence is from a Respiratory Syncytial Virus (RSV). In an exemplified embodiment, a nucleic acid (SEQ ID NO: 1) derived from RSV was immobilized on a porous silicon biochip of the invention. The biochip was then contacted with a probe or detector nucleic acid (SEQ ID NO: 2) having a sequence complementary to the immobilized nucleic acid (SEQ ID NO: 1) under conditions for selective hybridization of the nucleic acids. The complete genomic sequence of human RSV is known in the art (see, for example, Genbank accession number NC 001781) (SEQ ID NO: 3). Any sequence within SEQ ID NO: 3, or the complement thereof, that is of sufficient length and sequence for selective hybridization to an RSV nucleotide sequence is contemplated for use with the methods and materials of the present invention. Thus, all fragments and variants of the sequence shown in SEQ ID NO: 3, or the complementary sequence of SEQ ID NO: 3, are contemplated for use in the present invention.

Probes or detector nucleic acids of the invention can optionally comprise a detectable label or reporter molecule, such as fluorescent molecules, enzymes, radioactive moiety, and the like. Probes or detector nucleic acids of the invention can be of any suitable length for the method or assay in which they are being employed. Typically, probes or detector nucleic acids of the invention will be 10 to 500 or more nucleotides in length. Probes or detector nucleic acids that are 10 to 20, 21 to 30, 31 to 40, 41 to 50, 51 to 60, 61 to 70, 71 to 80, 81 to 90, 91 to 100, or 101 or more nucleotides in length are contemplated within the scope of the invention. In one embodiment, probes or detector nucleic acids are any of 9, 10, 11, 12, 13, 14, 15, 16, 17, 18, 19, 20, 21, 22, 23, 24, 25, 26, 27, 28, 29, 30, and so forth up to 100 nucleotides in length. Probes or detector nucleic acids of the invention can have complete (100%) nucleotide sequence identity with the polynucleotide sequence, or the sequence identity can be less than 100%. For example, sequence identity between a probe or detector nucleic acids and a sequence can be 99%, 98%, 97%, 96%, 95%, 90%, 85%, 80%, 75%, 70% or any other percentage sequence identity so long as the probe or detector nucleic acids can hybridize under stringent conditions to a nucleotide sequence of a target nucleic acid.

As used herein, the terms "nucleic acid," "polynucleotide," and "oligonucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. Polynucleotide sequences include the DNA strand sequence that is transcribed into RNA and the RNA strand that is translated into protein. The complementary sequence of any nucleic acid, polynucleotide, or oligonucleotide of the present invention is also contemplated within the scope of the invention. Polynucleotide sequences also include both full-length sequences as well as shorter sequences derived from the full-length sequences.

The subject invention also concerns variants of the polynucleotides of the present invention, including variants of the RSV sequence shown in SEQ ID NO: 3. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Polynucleotides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982).

Biochips of the invention have many advantages, including high responsiveness and selectivity, and are inexpensive. Two primary advantages make nanoscale porous silicon based DNA biochips a very attractive option: (i) enormous surface area, which ranges from about 90 to 783 m$^2$/cm$^3$, and which provide numerous sites for potential species to attach and (ii) its room temperature luminescence spans the visible spectrum which makes it an effective transducer. In one embodiment, binding DNA to porous silicon involves coating sol-gel material containing DNA on an oxidized silicon surface. Tetra-ethyl-ortho-silicate (TEOS) can be used to provide a stable coupling between two non-bonding surfaces: an inorganic surface to a bio-molecule (DNA). The most interesting feature of porous silicon is its room temperature visible luminescence. Porous silicon microcavity resonators possess the unique characteristics of line narrowing and luminescence enhancement (Canham, 1990). The emission peak position is completely tunable by modifying the coating over the surface of porous silicon (Lauerhans et al., 1993). The present invention demonstrates the optoelectronics properties of and the compatibility of the porous silicon fabrication process with the usual silicon technology. Further, a mechanical non-fluorescence based approach using AFM technique to detect DNA hybridization can be used with the present invention. In another embodiment, hybridization of sDNA with complementary DNA (cDNA) having a fluorescent probe molecule attached to the cDNA is utilized. Hybridization on the DNA biochip can be detected using photoluminescence technique. Results using a DNA biochip of the present invention and detection techniques are summarized in Tables 1-2. The present invention was found to be more sensitive, economical and time efficient than existing technologies as shown in Table 2.

Any element of any embodiment disclosed herein can be combined with any other element or embodiment disclosed herein as if the combination is explicitly disclosed or exemplified herein, and such combination is contemplated within the scope of the present invention.

All patents, patent applications, provisional applications, and publications referred to or cited herein are incorporated by reference in their entirety, including all figures and tables, to the extent they are not inconsistent with the explicit teachings of this specification.

Materials and Methods

Compositions and Reagents.

A crystalline n-type silicon wafer with resistivity ranging between 0.4 and 0.6 Ωcm was used for preparing porous silicon (PS) layers by dipping in a solution of hydrogen fluoride (HF) and ethanol. The target nucleic acid having DNA sequence 3'-GATCCTCGGTAACA CAGTACGATAC-CGTTTTGATTTACATGTCGTAGGT-TATTTTTAGCACCTTAGTATTTC TGTAAAAGATTGC-CCACGCTAATA-5' (SEQ ID NO: 1) and tetra-ethyl-ortho-silicate (TEOS), HCl, and HNO$_3$ were contacted with a porous silicon surface (prepared as described herein) for a sufficient period of time to permit the nucleic acid to bind thereto. Then, a detector nucleic acid labeled with a fluorescent molecule and having the complementary RSV F genome sequence 5'-CTAGGAGCCATTGTGTCATGCTATG-GCAAAACTAAATGTACAGCATC CAATAAAAATCGTGGAATCATAAAGA-CATTTTCTAACGGGTGCGATTAT-3' (SEQ ID NO: 2) was used for hybridization.

Preparation of Micro Cavities on Silicon Wafer.

With reference to FIG. 1, anodic etching was used to prepare porous silicon wafers using an electrolyte solution 12 containing 49% high purity aqueous HF and 50% ethanol. A 14.4 cm$^2$ exposed area of the polished, crystalline n-type silicon wafer 18 with resistivity ranging between 0.4 and 0.6 Ωcm was etched for 5 minutes in a Teflon cell 10 at a constant anodic current of 40.3 mA/cm$^2$. The cell 10 contains an O-ring 14.

A 200 nm gold layer was deposited by sputtering at the bottom of the silicon wafer 18 to ensure ohmic contact. The cathodic contact was made using a platinum mesh 16 that is in contact with the solution. After the etching process was achieved the wafer was rinsed in ethanol then blown dry in a nitrogen environment. The advantage of this cell geometry is the simplicity of equipment as shown in FIG. 1. The presence of a difference in the potential between the top and the bottom electrodes of such a cell, leads to different values of the local current density (Jarimaviciute et al., 2003).

Procedure of Immobilization of sDNA onto Porous Silicon.

The method used for binding DNA to the silicon involves coating the oxidized surface of porous silicon with a sol-gel containing single stranded DNA. Sol-gel is a colloidal suspension of silica particles that is gelled to form a solid. The resulting porous gel can be chemically purified and consolidated at high temperatures into high purity silica. The idea behind the sol-gel optical sensors is based on changes of optical parameters of active (sensing) molecules (DNA) physically entrapped in sol-gel thin films. Those changes are induced by changing external physico-chemical parameters such as temperature, hydrostatic pressure or presence of analyte molecules. There are several kinds of optical signals which could be used as analytical response of such sensors, for instance: intensity of light absorbed or emitted by the sensing molecules, time of luminescence decay (Chan, et al., 2000). Non-labeled DNA comprising the nucleotide sequence 3'-GATCCTCGGTAACACAGTACGATAC-CGTTTTGATTTACATGTCGTAGGT TATTTTTAGCAC-CTTAGTATTTCTGTAAAAGATTGCCCACGCTAATA-5' (SEQ ID NO: 1) was immobilized using tetraethylorthosilicate (TEOS) spread over the surface of the silicon wafer to immobilize DNA in the microcavities. A mixture of 25 µL of TEOS, 5 µL of 0.1 M HCl and 20 µL of de-ionized water (DI) were mixed in a vial (solution A). The last step involved mixing 2 µL single stranded DNA (sDNA) stock solution containing the oligonucleotide (SEQ ID NO: 1) and 3 µL DI water in 5 µL of solution A, resulting in a dilution of solution A to 50%. The pH was controlled near 7 during the mixing procedure described above. The single stranded DNA stock solution contains (1 mg) DNA in 1 mL DI water.

Figure 2:
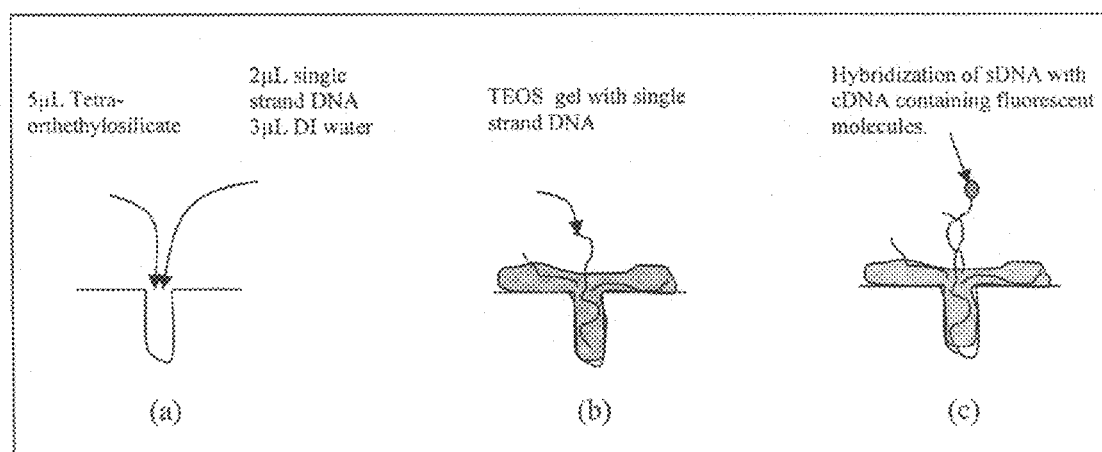
FIGS. 2A-2C show the preparation of DNA fixation and hybridization with fluorescent molecules on porous silicon (PS) using TEOS.

A schematic diagram is shown in FIGS. 2A-2C. FIG. 2A shows the procedure for immobilizing the sDNA on the porous silicon using TEOS. FIG. 2B shows the immobilized sDNA on porous silicon and FIG. 2C shows the hybridization of cDNA that corresponds to RSV F genome having the nucleotide sequence 5'-CTAGGAGCCATTGTGTCAT GCTATGGCAAAACTAAATGTACAGCATC-CAATAAAAATCGTGGAATCATAAAGACA TTTTCTAACGGGTGCGATTAT-3' (SEQ ID NO: 2). This complementary strand was labeled with a fluorescent molecule.

AFM Characterization of DNA Biochip.

There are various modes of atomic force microscope (AFM) operation, the most common are: Non-contact mode, contact mode, and tapping mode. Tapping mode is the preferred mode of operation in the case of this study since it has features that allow better quality imaging with little deleterious effects on the sample. Analysis of samples in such mode provides higher lateral resolutions, which is critical when analyzing DNA immobilized over a silicon surface. Lower forces and less damage to soft samples make it suitable for DNA structural analysis and sample scraping is virtually eliminated since there are minimal or no lateral forces exerted on the sample. General features of these molecules pertinent to important biological processes are now being characterized using this technique. AFM software is used to obtain quantitative, three-dimensional images of surfaces with ultra-high resolution. AFM provides measurements of surface roughness, grain size, and grain size distribution. All analyses were conducted in air and the samples were brought to room temperature before AFM analysis.

Optical Microscopic Studies of DNA Biochip.

Figure 4A:
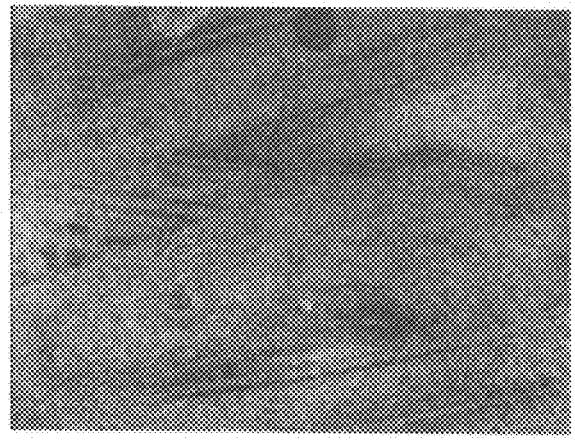
FIGS. 4A-4C show images of porous silicon with microcavities through Optical Microscopic investigation of DNA biochip.
Figure 4B:
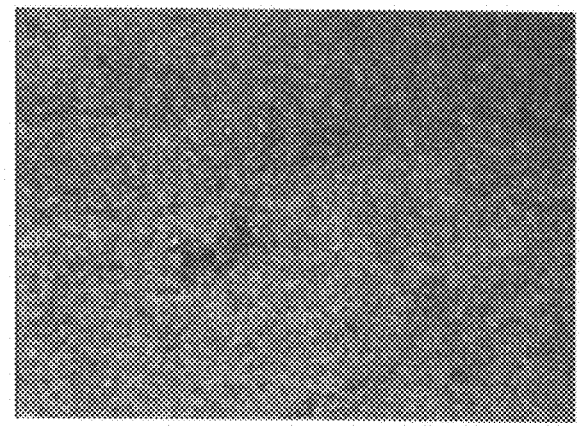
Figure 4C:
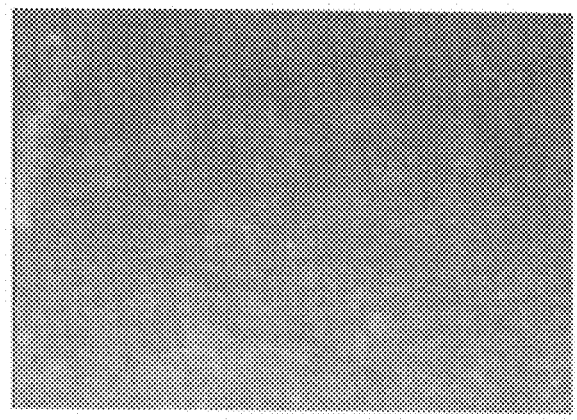
Figure 5A:
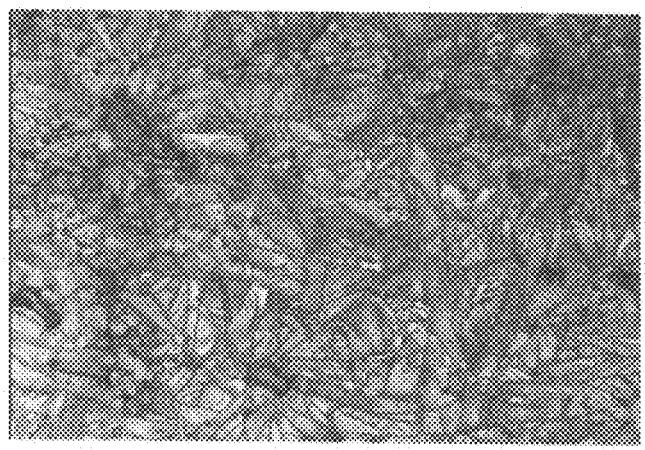
FIGS. 5A-5C show porous silicon microcavities attached with sDNA through Optical Microscopic investigation of DNA biochip.
Figure 5B:
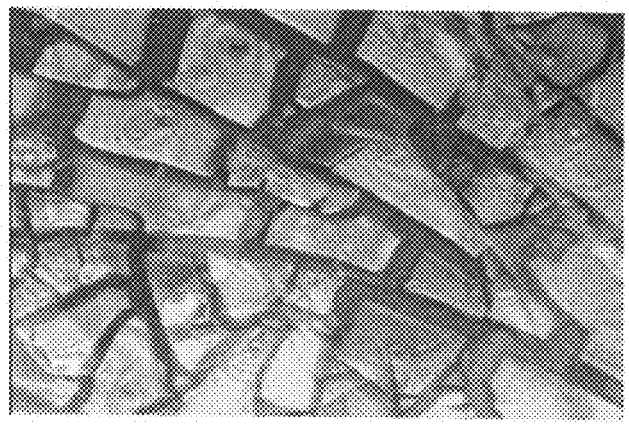
Figure 5C:
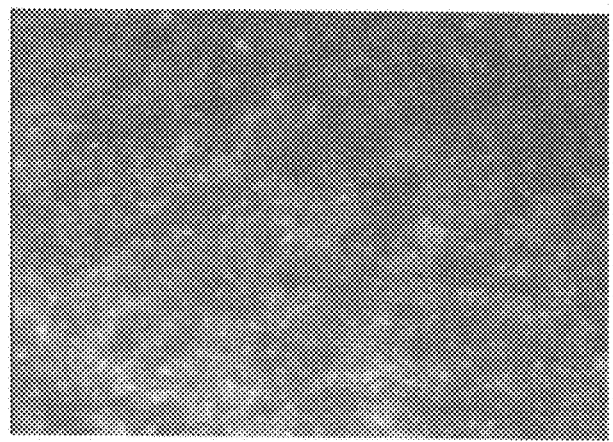
Figure 6A:
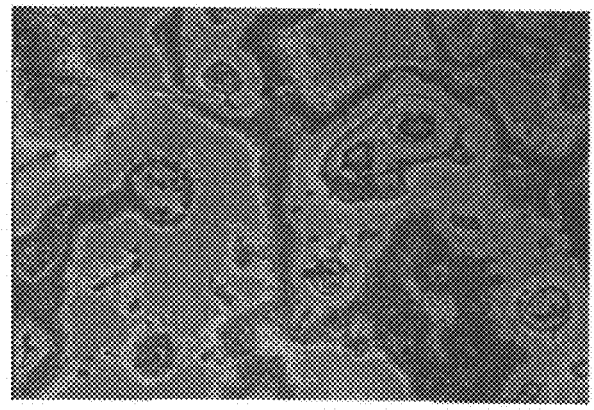
FIGS. 6A-6C show DNA hybridization with fluorescence attached cDNA molecule with sDNA through Optical Microscopic investigation of DNA biochip.
Figure 6B:
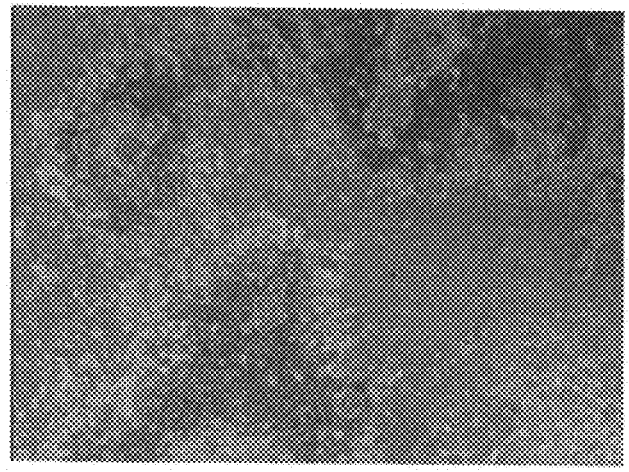
Figure 6C:
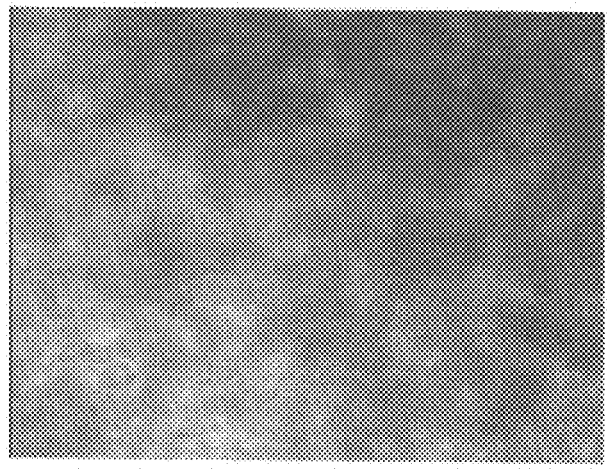

Optical microscopic pictures were recorded for porous silicon wafers and porous silicon containing sDNA and after hybridization of sDNA with cDNA. (FIGS. 4A-4C). The optical microscope of sDNA attached modified single-stranded oligonucleotides were recorded using a Vanox research grade optical microscope for homogeneous hybridization studies. The transverse mode profile for the disk and evanescent field used for sensing is equivalent to that of a slab waveguide with the same thickness and refractive indices. Therefore, one can take advantage of enhanced power at the surface of the porous silicon containing microcavities, having the same penetration depth and relative cladding power as in the straight waveguide structure.

Following are examples which illustrate procedures for practicing the invention. These examples should not be construed as limiting. All percentages are by weight and all solvent mixture proportions are by volume unless otherwise noted.

EXAMPLE 1

Preparation of Porous Silicon Wafer with Immobilized DNA

Porous silicon provides numerous sites for nucleic acid sequence to attach. The porous layer of silicon was fabricated by means of the electrochemical etching in HF solution. FIGS. 4A-4C show the surface of porous silicon after etching. In this case, only a small quantity of charge was generated to generate the pores over the silicon wafer surface. Single strand DNA (sDNA) (SEQ ID NO: 1) of RSV virus was immobilized on PS. A fluorescent probe molecule was attached to a cDNA (SEQ ID NO: 2) having a sequence complementary to the sequence in SEQ ID NO: 1 and then brought into contact with the PS having the sDNA immobilized thereon under conditions sufficient for hybridization of the cDNA to the immobilized sDNA. The fluorescent molecule on the cDNA provides the means of detecting the extent of hybridization of the cDNA to the sDNA.

EXAMPLE 2

SEM Characterization of Microcavities on Silicon Wafer

Figure 3:
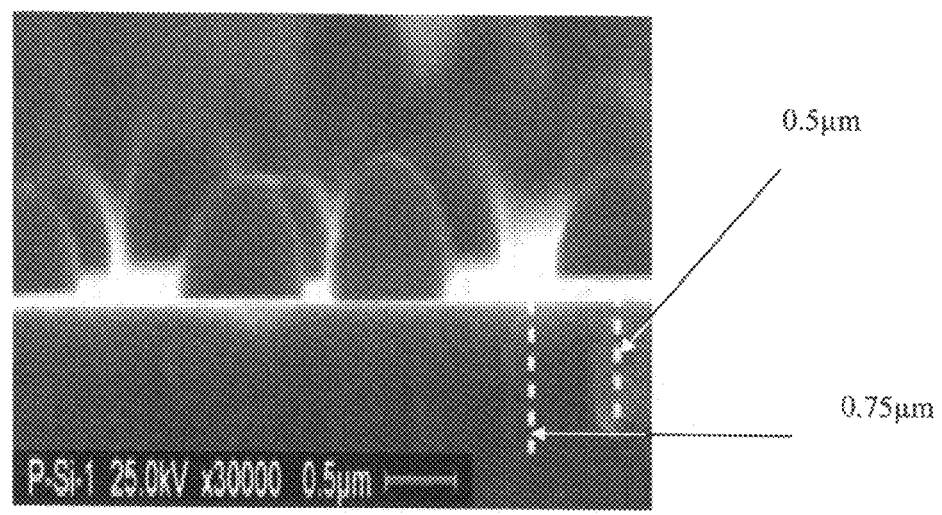
FIG. 3 shows an SEM picture of porous silicon.

A cross-section SEM picture of a porous silicon microcavity is shown in FIG. 3. This picture was taken transversally to the silicon surface and illustrates hemispherical structures over the entire surface. These structures represent the beginning stage of porous silicon formation. Furthermore, pore depths varying between 0.5 and 0.75 μm are highlighted in the figure by white-dotted lines.

EXAMPLE 3

Optical Microscopy (EPI) Studies of DNA Biochip

Epi indicates incident illumination and has been used in the present invention. The reflection and refraction of light according to the multiple wavelet concepts, now known as the Huygens' principle. When the wavefront encounters the interface between the two media, a portion of the light is reflected and another part is refracted. The periodic rows of miniature semicircular red waves represent the Huygens wavelets that together compose the incident and reflected wave fronts. Wavelets that penetrate the media boundary to become refracted are portrayed in blue, as is the line passing through the center of the refracted beam that denotes their direction of propagation. According to the Huygens model of light, a small portion of each angled wavefront impacts the second medium before the rest of the front reaches the interface. This portion of the wavefront begins to move through the second medium while the rest of the wave is still traveling in the first medium. The speed at which the wavelets travel through is dependent on the refractive indices of the media. If the second medium has a higher refractive index than the first, then the light slows down, and vice versa. Since in either case the wavefront is then traveling at two different speeds, it bends into the second medium, thus changing the angle of propagation. The most common oil-immersion objective in use in routine microscopy is used for magnification of ×100. Fluorescence is a process where a substance after having absorbed light (photons) emits a radiation the wavelength (colour) of which is longer than that of the absorbed light, and where this emission stops immediately after cessation of the excitation. This phenomenon is used to understand the DNA hybridization in DNA biochip. Besides the "classical" excitation of fluorescence in a light microscope it is possible today to obtain the same emission effect. Fluorescence occurs either as autofluorescence of biological and/or inorganic structures or as so called secondary fluorescence after a treatment of the specimen with special dyes (e.g., fluorochromes, fluorescent markers). The microcavity design has an advantage over the single layer structure as the refractive index of the surrounding material increases the reflectivity spectrum to shift. A blue shift is predicted because the pores are filled with sol-gel material with different refractive index as shown in FIGS. 4A-4C. This is further demonstrated during the optical microscopy studies. A optical microscope was used to achieve fluorescence-aided molecule sorting (FAMS) and enabled simultaneous analysis of DNA interactions at the level of a single strand. This was performed by labeling cDNA (SEQ ID NO: 1) corresponding to RSV F genomic sequence. The cDNA probe comprised the nucleotide sequence 5'-CTAGGAGCCATTGTGTCATGCTATG-GCAAAACTAAATGTACAGCATCCA ATAAAAATCGTGGAATCATAAAGA-CATTTTCTAACGGGTGCGATTAT-3' (SEQ ID NO:2) and was used for hybridization. This complementary strand was labeled with a fluorescent molecule that serves as donor-acceptor pair for a Forster resonance energy transfer. FAMS permits equilibrium and kinetic analysis of macromolecule-ligand interactions; this was validated by measuring with sDNA and cDNA. FAMS is a general platform for ratio metric measurements that report on structure, dynamics, stoichiometries, environment, and interactions of diffusing or immobilized molecules, thus enabling detailed mechanistic studies and ultra sensitive diagnostics (Garcia-Parajo et al., 2001).

EXAMPLE 4

UV Studies of DNA Biochip

UV-spectra have shown the retention of the fluorophore in the modified cDNA. The absorbance at 333-340 nm and at 260 nm due to fluorophore and DNA, respectively, and fluorescence emission spectra at 500-520 nm wavelengths clearly confirmed the retention of the chromophore in the oligonucleotides. The relative enhancement in the intensity of peak is due to the fluorescence molecule attached to cDNA. A fluorophore layer placed on top of porous silicon will experience an enhancement of the input optical signal. The effect of field enhancement in microcavities can be interpreted as an increase of absorption efficiency of the fluorophore due to increased interaction length of the incident field with an absorbing molecule. Therefore, an increase in amount of fluorescent photons generated from the molecule at the microcavities versus the linear waveguide is proportional to a number of fluorescence molecule or hybridization with cDNA. Therefore, the advantage of the microcavity format versus waveguide format for analytical applications is the amount of fluorescence molecules present at surface of porous silicon or hybridization. Therefore, the fluorescence signal from the molecules near the microcavity is increased

EXAMPLE 5

Figure 7A:
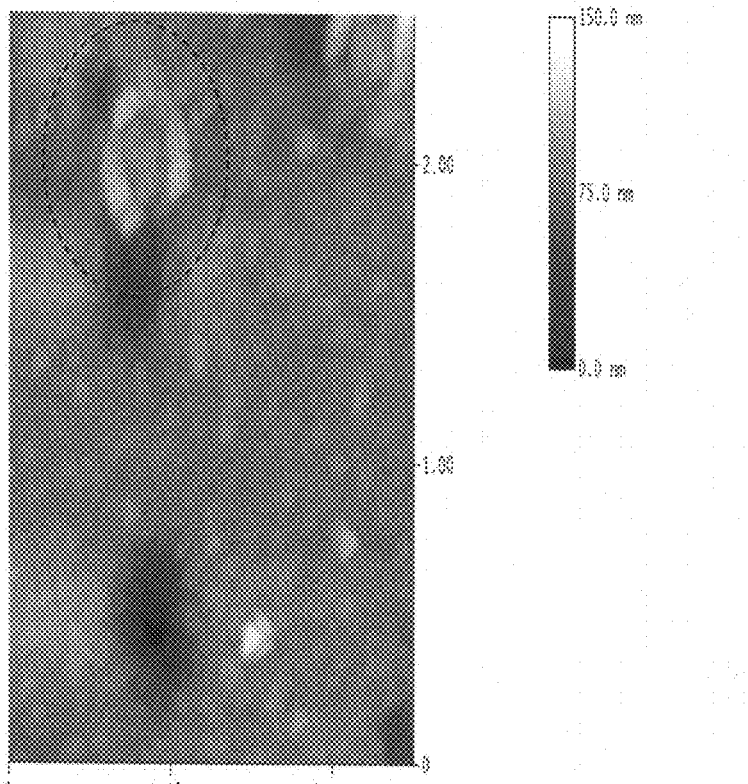
FIG. 7A shows single stranded DNA attached to microcavity and FIG. 7B shows a magnified view of single stranded DNA attached to microcavity.
Figure 7B:
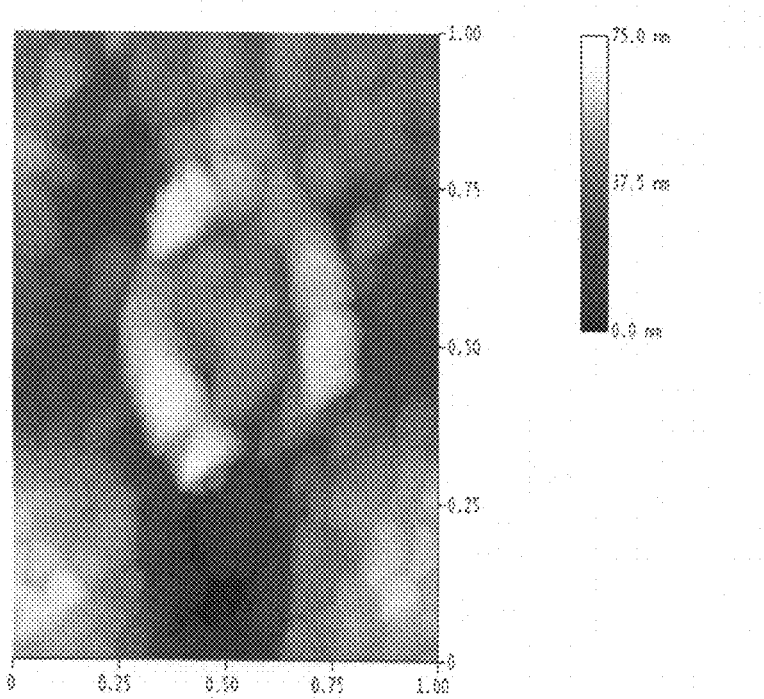

AFM Studies of DNA Biochiop-AFM Surface Analysis of DNA Immobilized on Microporous Cavity Surface images of non-hybridized sDNA on PS and sDNA hybridized with an RSV F specific oligonucleotide cDNA probe were taken using a Digital Instruments Atomic Force Microscope (AFM) equipped with nanoscope dimension 3000 software. FIGS. 7A and 7B show a two dimensional picture of a section of the microporous silicon wafer with a single strand DNA bundle attached to a cavity. FIGS. 7A and 7B show a "horse shoe" like structure coming out of the microcavity.

Figure 8A:
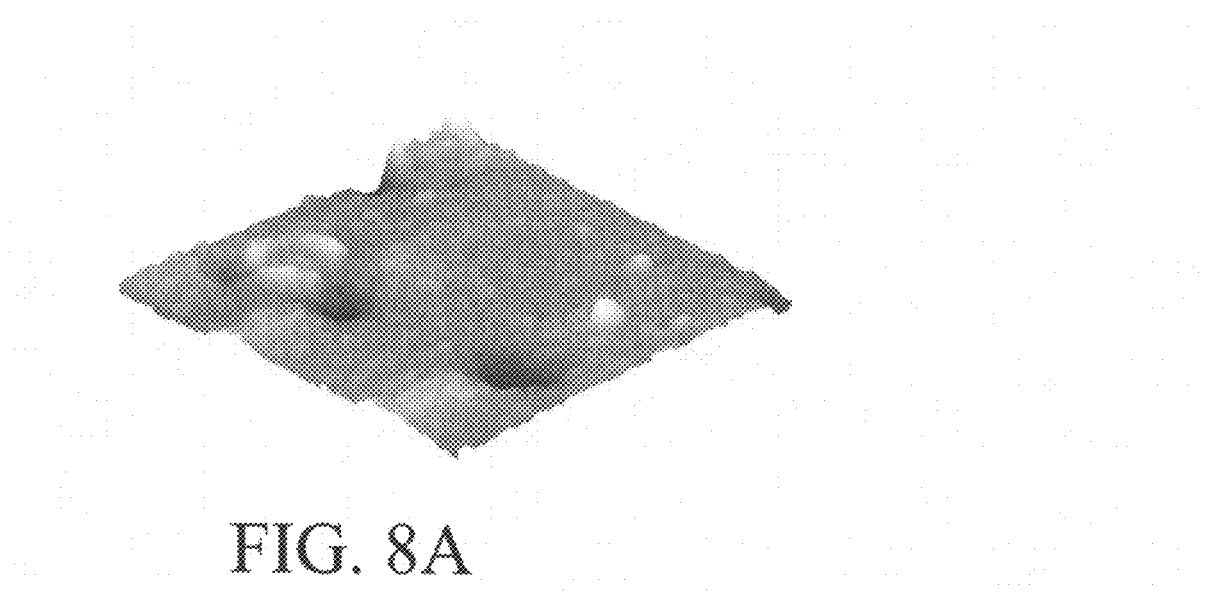
FIG. 8A shows a 3D AFM picture of an sDNA bundle attached to microcavity on silicon wafer and FIG. 8B shows an AFM Images analysis of DNA hybridization (interaction of sDNA with cDNA.
Figure 8B:
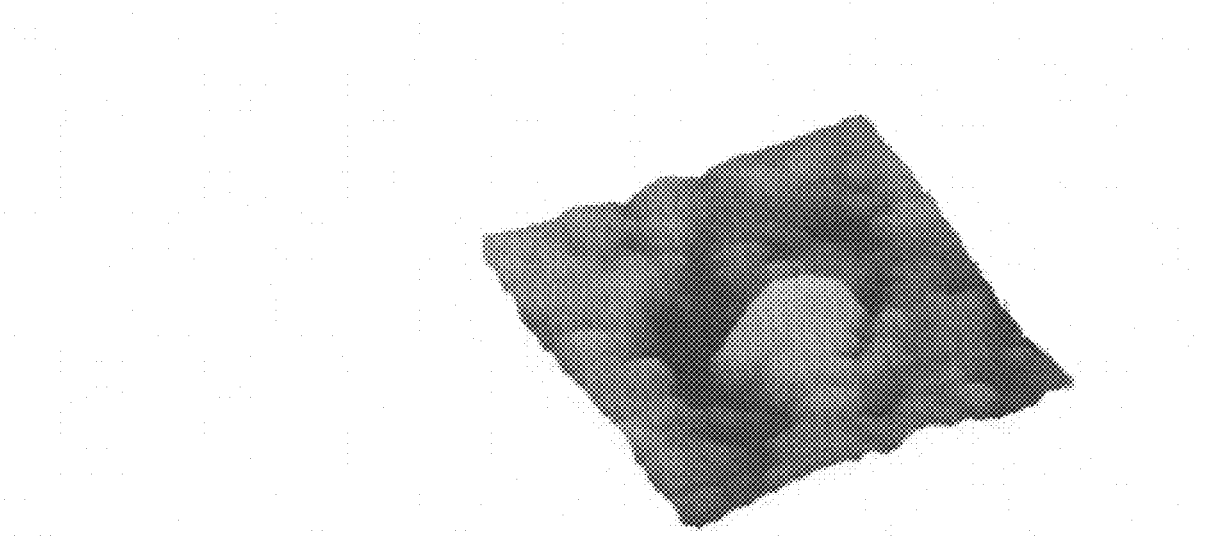

FIG. 8A confirms the sDNA bundle shape and provides a better image of the surface profile of the sol gel/sDNA mixture. Further 3D AFM analysis of this image provides more information about the dimensions and the form of the ssDNA bundle, as shown in FIG. 8A. In FIG. 8B notice that this value is at least twice as shallow as the value determined by SEM. This is due to the application of the sol gel film which has partially filled the microcavities.

EXAMPLE 6

Photoluminescence Studies of RSV DNA Before and After Hybridization

Figure 9:
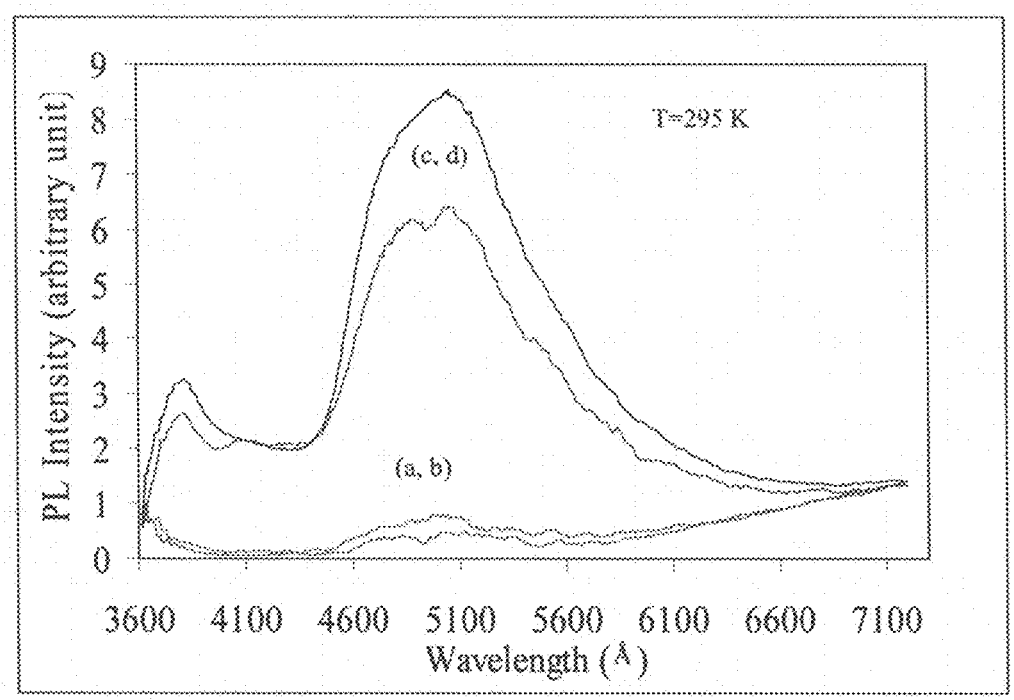
FIG. 9 shows PL spectra of: sample "a" and "b" (sDNA on porous silicon), and PL spectra of sample "c" and "d" (cDNA hybridized to sDNA on porous silicon).

Photoluminescence (PL) was used to study the effectiveness with which the fluorescently tagged RSV oligonucleotide probe molecules hybridize to the fixed sDNA molecules on the surface of the porous silicon. Four samples were selected for this study: two (samples "a" and "b") with sDNA only immobilized on the surface and two hybridized samples having the oligonucleotide probe hybridized to the sDNA (samples "c" and "d"). All samples were illuminated with a helium cadmium (He Cd) laser at 325 nm and 55 mW. The laser beam was kept at 1.5 mm in diameter to minimize the damage to the DNA molecules. FIG. 9 shows the PL spectra of sDNA fixed on two different "sDNA only" samples (a, b), and two hybridized DNA samples (c, d). A clear increase in the PL intensity was observed after hybridization of the single strand DNA with the RSV cDNA.

FIG. 9 shows that all peaks are found around 505 nm with minor shifting in the wave length in the order of 5 to 10 nm between the sDNA samples and the hybridized ones. However a significant change in the intensity was clearly perceived between sDNA and hybridized DNA samples. While sDNA only samples (a, b) did not show any significant peak, the hybridized (c, d) samples did show two peaks. The smaller peak was registered at 382 nm which corresponds to the color blue. The peak with higher intensity corresponds to the green color with a wavelength of 508 nm. This clearly demonstrates a noticeable change that could be used to quantify the extent of hybridization on the surface. Furthermore, the PL spectra are in concordance with the images obtained by fluorescent microscopy, where bright blue and green areas were observed on the surface of the PS having the cDNA hybridized thereon.

TABLE 1

Fluorescence and optical microscopic studies of DNA biochip.

| Technique | sDNA | Hybridized (sDNA:cDNA) |
| --- | --- | --- |
| Optical Microscopy | Dark green color was observed with very little fluorescence observed | Bright blue and green fluorescence observed |
| Mass difference (AFM) | "Horse shoe" like sDNA bundles were found | Hybridized DNA structure with twice the sDNA images were observed |
| Photoluminescence Studies (PL) | No significant photoluminescence was observed | Relatively high intensity spectra with blue peak (382 nm) and green peak (508 nm) |

TABLE 2

Comparison of existing RSV detection techniques with DNA biochip of present invention.

| Techniques | Time of detection | Selectivity | Sensitivity | Reference |
| --- | --- | --- | --- | --- |
| Radioimmunoassay | Days | Likely to be positive | 79% | Meurman et al., 1984a |
| Immunofluorescence (Serology) | Days | Lower background absorbance can be obtained if the RSV antigen is partially purified | 75% | Walliver et al., 1980 |
| CF Assays | Days | 5-6% sensitivity | 25% | Richardson et al., 1978 |
| ELISA | Days | 88% selectivity | 92% | Meurman, et al. 1984b |
| DNA Biochip | <Minutes | Highly selective | 100% | Present work |

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 6,495,352
U.S. Pat. No. 6,303,290

Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Brinker, C. J. et al. (1985) *J Non-Crystalline Solids.* 70:301-322.
Broude, N. E. (2002) "Stem loop oligonucleotides:a robust tool for molecular biology and biotechnology" *TIBTECH* 20:249-256.
Canham, L. T. et al. (1990) *Appl. Phy Lett.* 37:1046.
Chan, S. et al. (2000) *Phys. Sta. Sol* 182:541.
Cluzel, Ph. et al. (1996) *Science* 271:792-794.
Drobyshov, A. N. et al. (1997) *Gene* 188:45-52.
Fink, H. W. et al. (1999) *Science* 398:407-410.
Fritz, J. et al. (2000) *Single Mol.* 1:1,53-58.
Garcia-Parajo, M. F. et al. (2001) *Chem Phys Chem* 2(6):347-360.
Goryachev, D. N. et al. (2003) *Semiconductors* 37(4):477-481.
Guckenberger, R. et al. (1994) *Science* 266:1538-1540.
Hansma, H. G. et al. (1991) *Nucleic Acids Res.* 20:3585-3590.
Hench, L. L. et al. (1990) *Chem. Rev.* 90:35-40.
Isola, N. et al. (1998) *Anal. Chem.* 70:1352.
Lauerhans, J. M. et al. (1993) *Science* 261:1567.
Janshoff, A. et al. (1998) *J. Amer. Chem. Soc.* 120:12108.
Jarimaviciute-Zvalioniene, R. et al. (2003) *Material Science* 9:317-320.
Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecular Sequences" *Proc. Natl. Acad. Sci. USA* 90:5873-5877.
Kumar, A. et al. (2000) *Analytica Chimica Acta,* 414(1-2):43-50.
Lakowicz, J. R. (1999) "Principles of Fluorescence Spectroscopy", Kluwer Academic/Plenum Press, New York.
Maniatis, T., E. F. Fritsch, J. Sambrook (1982) *Molecular Cloning: A Laboratory Manual*, Cold Spring Harbor Laboratory, Cold Spring Harbor, N.Y.
Meurman, O. et al. (1984a) *J. Med Virol.* 14:61-65.
Meurman, O. et al. (1984b) *J. Med. Virol.*14:67-72.

Mirzabekov, A. D. (1994) "DNA sequencing by hybridization a mega sequencing method and a diagnostic tool" *TIBTECH* 12:27-32.
Richardson, L. S. et al. (1978) *Infect. Immun.* 20:660-664.
Schena, M. (2000) *Microarraybiochip Technology*, Eaten Publishing Natick Mass.
Selvein, P. R. (2000) *Nat. Struct. Biol.* 730-734.
Singh, Y. et al. (2000) *Curr. Sci* 78:487-492.
Smith, S. B. et al. (1992a) Science 258:1122-1126.
Smith, R. L. et al. (1992b) *J. Appl. Phy* 71(8):1-22.
Smith, S. B. et al. (1996) *Science* 271:795-799.
Speel, E. J. M. et al. (1999) *Cytochem.* 47:281-288.
Strick, T. R. et al. (1996) *Science* 271:1835-1837.
Uhlir, A. (1956) *Bell Syst. Tech. J.* 35:333.
Walliver, R. et al. (1980) *J. Pediatr.* 96: 808-813.
Wang, D. W. et al. (1997) *J. Biophys.* 71:1335-1346.
Wannmalm, S. et al. (1997) *Proc. Natl. Acad. Sci.* 94:10641-10646.
Wittwer, C. T. et al. (1997) *Biotechniques* 22:130-1,134-8.
Yanagida, M., Hiraoka, Y., Katsura, I. (1983) *Cold Spring Harbor Symp. Quant Biol.* 47:177.
Yang, T. T. et al. (1996) "Optimized Codon Usage and Chromophore Mutations Provide Enhanced Sensitivity with the Green Fluorescent Protein" *Nucleic Acid Research* 24(22): 4592-4593.
Genbank accession number NC 001781

We claim:

1. A method for detecting a target nucleic acid comprising the steps of:
   a) contacting a silicon-based biochip with a nucleic acid containing sample to be tested for the presence of the target nucleic acid, wherein said biochip comprises a silicon wafer comprising a bottom layer that provides ohmic contact and said biochip further comprising microcavities in said silicon wafer, and wherein said nucleic acid is contacted with the surface of said silicon wafer of said biochip in the presence of tetra-ethyl-ortho-silicate (TEOS), wherein nucleic acid present in said sample binds to and becomes immobilized on the surface of said silicon wafer of said biochip;
   b) contacting said biochip with a detector nucleic acid that comprises a nucleotide sequence that is substantially complementary with the sequence of said target nucleic acid under conditions that permit hybridization of the detector nucleic acid to the target nucleic acid and wherein nucleic acid that does not have a nucleotide sequence substantially complementary with the nucleotide sequence of the target nucleic acid does not hybridize to the target nucleic acid; and
   c) detecting said detector nucleic acid hybridized to nucleic acids immobilized on the surface of said silicon wafer of said biochip.

2. The method according to claim 1, wherein said sample to be tested for the presence of a target nucleic acid is provided on the surface of said silicon wafer of said biochip in a sol-gel composition.

3. The method according to claim 1, wherein said method further comprises washing said biochip to remove unbound nucleic acid.

4. The method according to claim 1, wherein said detector nucleic acid comprises a detectable label.

5. The method according to claim 4, wherein said detectable label is selected from the group consisting of an enzyme, a prosthetic group, a fluorescent material, a luminescent material, a bioluminescent material, and a radioactive material.

6. The method according to claim 5, wherein said fluorescent material is selected from the group consisting of umbelliferone, fluorescein, fluorescein isothiocyanate, Cascade Blue, rhodamine, dichlorotriazinylamine fluorescein, dansyl chloride, Texas Red, Oregon Green, cyanine, allophycocyanine or phycoerythrin.

7. The method according to claim 5, wherein said luminescent material is luminol.

8. The method according to claim 5, wherein said bioluminescent material is selected from the group consisting of luciferase, luciferin, green fluorescent protein, enhanced green fluorescent protein, or aequorin.

9. The method according to claim 1, wherein hybridization of the detector nucleic acid to said target nucleic acid is detected using atomic force microscopy (AFM), scanning electron microscopy, UV visible spectroscopy, fluorescence microscopy, or photoluminescence spectroscopy.

10. The method according to claim 1, wherein said hybridization is conducted under stringent conditions.

11. The method according to claim 1, wherein said target nucleic acid is from a Respiratory Syncytial Virus (RSV).

12. The method according to claim 11, wherein said detector nucleic acid comprises the nucleotide sequence shown in SEQ ID NO: 1 or SEQ ID NO: 2, or a fragment of said nucleotide sequence capable of selective hybridization with said target nucleic acid.

13. The method of claim 1, wherein hybridization of the detector nucleic acid to said target nucleic acid is detected using atomic force microscopy (AFM).

14. The method of claim 1, wherein said detector nucleic acid is 10 to 20, 21 to 30, 31 to 40, 41 to 50, 51 to 60, 61 to 70, 71 to 80, 81 to 90, or 91 to 100 nucleotides in length.

15. The method of claim 1, wherein said microcavities have a depth of from about 0.5 µm to about 0.75 µm.

16. The method of claim 1, wherein said detector nucleic acid is labeled with a first moiety that can bind to or be bound by a second moiety, wherein said second moiety comprises a detectable label, or said second moiety can bind to or be bound by a moiety having a detectable label.

17. The method of claim 1, wherein said bottom layer comprises gold.

18. A method for detecting a target nucleic acid comprising the steps of:
   a) contacting a silicon-based biochip with a detector nucleic acid that comprises a nucleotide sequence that is substantially complementary with the sequence of said target nucleic acid under conditions that permit hybridization of the detector nucleic acid to said target nucleic acid and wherein nucleic acid that does not have a nucleotide sequence substantially complementary with the nucleotide sequence of the target nucleic acid does not hybridize to the target nucleic acid, wherein said biochip comprises a silicon wafer comprising a bottom layer that provides ohmic contact and said biochip further comprising microcavities in said silicon wafer, and wherein the surface of said silicon wafer of said biochip has immobilized thereon nucleic acid from a sample being tested for the presence of said target nucleic acid, wherein said nucleic acid is immobilized on the surface of said silicon wafer of said biochip surface in the presence of tetra-ethyl-ortho-silicate (TEOS); and
   b) detecting said detector nucleic acid hybridized to nucleic acids immobilized on the surface of said silicon wafer of said biochip.

19. The method according to claim 18, wherein said sample to be tested for the presence of a target nucleic acid is provided on the surface of said silicon wafer of said biochip in a sol-gel composition.

20. The method according to claim 18, wherein said method further comprises washing said biochip to remove unbound nucleic acid.

21. The method according to claim 18, wherein said detector nucleic acid comprises a detectable label.

22. The method according to claim 21, wherein said detectable label is selected from the group consisting of an enzyme, a prosthetic group, a fluorescent material, a luminescent material, a bioluminescent material, and a radioactive material.

23. The method according to claim 22, wherein said fluorescent material is selected from the group consisting of umbelliferone, fluorescein, fluorescein isothiocyanate, Cascade Blue, rhodamine, dichlorotriazinylamine fluorescein, dansyl chloride, Texas Red, Oregon Green, cyanine, allophycocyanine or phycoerythrin.

24. The method according to claim 22, wherein said luminescent material is luminol.

25. The method according to claim 21, wherein said bioluminescent material is selected from the group consisting of luciferase, luciferin, green fluorescent protein, enhanced green fluorescent protein, or aequorin.

26. The method according to claim 18, wherein hybridization of the detector nucleic acid to said target nucleic acid is detected using atomic force microscopy (AFM), scanning electron microscopy, UV visible spectroscopy, fluorescence microscopy, or photoluminescence spectroscopy.

27. The method according to claim 18, wherein hybridization is conducted under stringent conditions.

28. The method according to claim 18, wherein said target nucleic acid is from a Respiratory Syncytial Virus (RSV).

29. The method according to claim 28, wherein said detector nucleic acid comprises the nucleotide sequence shown in SEQ ID NO: 2, or a fragment of said nucleotide sequencecapable cable of selective hybridization with said target nucleic acid.

30. The method of claim 18, wherein hybridization of the detector nucleic acid to said target nucleic acid is detected using atomic force microscopy (AFM).

31. The method of claim 18, wherein said detector nucleic acid is 10 to 20, 21 to 30, 31 to 40, 41 to 50, 51 to 60, 61 to 70, 71 to 80, 81 to 90, or 91 to 100 nucleotides in length.

32. The method of claim 18, wherein said microcavities have a depth of from about 0.5 µm to about 0.75 µm.

33. The method of claim 18, wherein said detector nucleic acid is labeled with a first moiety that can bind to or be bound by a second moiety, wherein said second moiety comprises a detectable label, or said second moiety can bind to or be bound by a moiety having a detectable label.

34. The method of claim 18, wherein said bottom layer comprises gold.

* * * * *

UNITED STATES PATENT AND TRADEMARK OFFICE
CERTIFICATE OF CORRECTION

PATENT NO. : 7,875,426 B2
APPLICATION NO. : 11/347438
DATED : January 25, 2011
INVENTOR(S) : Arun Kumar et al.

Page 1 of 1

It is certified that error appears in the above-identified patent and that said Letters Patent is hereby corrected as shown below:

Column 32,
Lines 6-7, "shown in SEQ ID NO: 2" should read --shown in SEQ ID NO: 1 or SEQ ID NO: 2--.

Lines 7-8, "sequencecapable cable of" should read --sequence capable of--.

Signed and Sealed this
Twenty-sixth Day of April, 2011

David J. Kappos
*Director of the United States Patent and Trademark Office*

```
                              SEQUENCE LISTING

<160> NUMBER OF SEQ ID NOS: 3

<210> SEQ ID NO 1
<211> LENGTH: 96
<212> TYPE: DNA
<213> ORGANISM: Human Respiratory Syncytial Virus

<400> SEQUENCE: 1
ataatcgcac ccgttagaaa atgtctttat gattccacga tttttattgg atgctgtaca     60
tttagttttg ccatagcatg acacaatggc tcctag                               96

<210> SEQ ID NO 2
<211> LENGTH: 96
<212> TYPE: DNA
<213> ORGANISM: Human Respiratory Syncytial Virus

<400> SEQUENCE: 2
ctaggagcca ttgtgtcatg ctatggcaaa actaaatgta cagcatccaa taaaaatcgt     60
ggaatcataa agacattttc taacgggtgc gattat                               96

<210> SEQ ID NO 3
<211> LENGTH: 15225
<212> TYPE: DNA
<213> ORGANISM: Human Respiratory Syncytial Virus

<400> SEQUENCE: 3
acgcgaaaaa atgcgtacta caaacttgca cattcggaaa aaatggggca aataagaatt     60
tgataagtgc tatttaagtc taaccttttc aatcagaaat ggggtgcaat tcactgagca    120
tgataaaggt tagattacaa aatttatttg acaatgacga agtagcattg ttaaaaataa    180
catgttatac tgacaaatta attcttctga ccaatgcatt agccaaagca gcaatacata    240
caattaaatt aaacggtata gtttttatac atgttataac aagcagtgaa gtgtgccctg    300
ataacaacat tgtagtaaaa tctaacttta caacaatgcc aatattacaa aacggaggat    360
acatatggga attgattgag ttgacacact gctctcaatt aaacggtcta atggatgata    420
attgtgaaat caaatttttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gacccctgtc gatggattca ataataacat ctctcaccaa    720
agaaatcatc acacacaaat tcatatactt gataaacaat gaatgtattg taagaaaact    780
```

```
tgatgaaaga caagctacat ttacattctt agtcaattat gagatgaagc tactgcacaa      840
agtagggagt accaaataca agaaatacac tgaatataat acaaaatatg gcactttccc      900
catgcctata tttatcaatc atggcgggtt tctagaatgt attggcatta agcctacaaa      960
acacactcct ataatataca aatatgacct caacccgtaa attccaacaa aaaaaaccaa     1020
cccaaccaaa ccaagctatt cctcaaacaa caatgctcaa tagttaagaa ggagctaatc     1080
cgttttagta attaaaaata aaagtaaagc caataacata aattgggca aatacaaaga     1140 tggctcttag caaagtcaag ttaaatgata cattaaataa ggatcagctg ctgtcatcca     1200
gcaaatacac tattcaacgt agtacaggag ataatattga cactcccaat tatgatgtgc     1260
aaaaacacct aaacaaacta tgtggtatgc tattaatcac tgaagatgca atcataaat     1320 tcacaggatt aataggtatg ttatatgcta tgtccaggtt aggaagggaa gacactataa     1380
agatacttaa agatgctgga tatcatgtta aagctaatgg agtagatata acaacatatc     1440
gtcaagatat aaatgaaag gaaatgaaat tcgaagtatt aacattatca agcttgacat     1500
cagaaataca agtcaatatt gagatagaat ctagaaaatc ctacaaaaaa atgctaaaag     1560
agatgggaga agtggctcca gaatataggc atgattctcc agactgtggg atgataatac     1620
tgtgtatagc agcacttgta ataaccaaat tagcagcagg agacagatca ggtcttacag     1680
cagtaattag gagggcaaac aatgtcttaa aaaatgaaat aaaacgctac aagggtctca     1740
taccaaagga tatagctaac agtttttatg aagtgtttga aaaacaccct catcttatag     1800
atgtttttgt gcactttggc attgcacaat catcaacaag agggggtagt agagttgaag     1860
gaatctttgc aggattgttt atgaatgcct atggttcagg gcaagtaatg ctaagatggg     1920
gagttttagc caaatctgta aaaaatatca tgctaggtca tgctagtgtc caggcagaaa     1980
tggagcaagt tgtggaagtc tatgagtatg cacagaagtt gggaggagaa gctggattct     2040
accatatatt gaacaatcca aaagcatcat tgctgtcatt aactcaattt cctaacttct     2100
caagtgtggt cctaggcaat gcagcaggtc taggcataat gggagagtat agaggtacgc     2160 caagaaaacca ggatctttat gatgcagcca aagcatatgc agagcaactc aaagaaaatg     2220
gagtaataaa ctacagtgta ttagacttaa cagcagaaga attggaagcc ataaagaatc     2280
aactcaaccc taaagaagat gatgtagagc tttaagttaa caaaaaatac ggggcaaata     2340
agtcaacatg gagaagtttg cacctgaatt tcatggagaa gatgcaaata caaagctac     2400 caaattccta gaatcaataa agggcaagtt cgcatcatcc aaagatccta agaagaaaga     2460
tagcataata tctgttaact caatagatat agaagtaacc aaagagagcc cgataacatc     2520
tggcaccaac atcatcaatc caacaagtga agccgacagt accccagaaa ccaaagccaa     2580
ctacccaaga aaacccctag taagcttcaa agaagatctc accccaagtg caacccttt     2640 ttctaagttg tacaaagaaa caatagaaac atttgataac aatgaagaag aatctagcta     2700
ctcatatgaa gagataaatg atcaaacaaa tgacaacatt acagcaagac tagatagaat     2760
tgatgaaaaa ttaagtgaaa tattaggaat gctccataca ttagtagttg caagtgcagg     2820
acccacttca gctcgcgatg gaataagaga tgctatggtt ggtctgagag aagaaatgat     2880
agaaaaaata agagcggaag cattaatgac caatgatagg ttagaggcta tggcaagact     2940
taggaatgag gaaagcgaaa aaatggcaaa agacacctca gatgaagtgc ctcttaatcc     3000
aacttccaaa aaattgagtg acttgttgga agacaacgat agtgacaatg atctgtcact     3060
tgatgatttt tgatcagtga tcaactcact cagcaatcaa caacatcaat aaaacagaca     3120
tcaatccatt gaatcaactg ccagaccgaa caaacaaatg tccgtcagcg gaaccaccaa     3180
```

```
ccaatcaatc aaccaactga tccatcagca acctgacgaa attaacaata tagtaacaaa    3240
aaaagaacaa gatggggcaa atatggaaac atacgtgaac aagcttcacg aaggctccac    3300
atacacagca gctgttcagt acaatgttct agaaaaagat gatgatcctg catcactaac    3360
aatatgggtg cctatgttcc agtcatctgt accagcagac ttgctcataa agaacttgc    3420 aagcatcaac atactagtga agcagatctc tacgcccaaa ggaccttcac tacgagtcac    3480
gattaactca agaagtgctg tgctggctca aatgcctagt aatttcatca taagcgcaaa    3540
tgtatcatta gatgaaagaa gcaaattagc atatgatgta actacacctt gtgaaatcaa    3600
agcatgcagt ctaacatgct aaaagtgaa aagtatgtta actacagtca aagatcttac    3660
catgaagaca ttcaaccccca ctcatgagat cattgctcta tgtgaatttg aaaatattat    3720
gacatcaaaa agagtaataa taccaaccta tctaagacca attagtgtca aaacaagga    3780 tctgaactca ctagaaaaca tagcaaccac cgaattcaaa aatgctatca ccaatgcgaa    3840
aattattccc tatgctggat tagtattagt tatcacagtt actgacaata aaggagcatt    3900
caaatatatc aagccacaga gtcaatttat agtagatctt ggtgcctacc tagaaaaaga    3960
gagcatatat tatgtgacta ctaattggaa gcatacagct acacgttttt caatcaaacc    4020
actagaggat taaatttaat tatcaacact gaatgacagg tccacatata tcctcaaact    4080
acacactata tccaaacatc atgaacatct acactcacac cttcatcaca caaaccaatc    4140
ccactcaaaa tccaaaatca ctaccagcca ctatctgcta gacctagagt gcgaataggt    4200
aaataaaacc aaaatatggg gtaaatagac attagttaga gttcaatcaa tctcaacaac    4260
catttatacc gccaattcaa tacatatact ataaatctta aaatgggaaa tacatccatc    4320
acaatagaat tcacaagcaa attttggccc tattttacac taatacatat gatcttaact    4380
ctaatctctt tactaattat aatcactatt atgattgcaa tactaaataa gctaagtgaa    4440
cataaaacat tctgtaacaa tactcttgaa ctaggacaga tgcatcaaat caacacatag    4500
tgctctacca tcatgctgtg tcaaattata atcctgtata tataaacaaa caaatccaat    4560
cttctcacag agtcatggtg tcgcaaaacc acgccaacta tcatggtagc atagagtagt    4620
tatttaaaaa ttaacataat gatgaattat tagtatggga tcaaaaacaa cattggggca    4680
aatgcaacca tgtccaaaca caagaatcaa cgcactgcca ggactctaga aaagacctgg    4740
gatactctca atcatctaat tgtaatatcc tcttgtttat acagattaaa tttaaaatct    4800
atagcacaaa tagcactatc agttctggca atgataatct caacctctct cataattgca    4860
gccataatat tcatcatctc tgccaatcac aaagttacac taacaacggt cacagttcaa    4920
acaataaaaa accacactga aaaaacatc accacctacc ttactcaagt cccaccagaa    4980
agggttagct catccaaaca acctacaacc acatcaccaa tccacacaaa ttcagccaca    5040
acatcaccca acacaaagtc agaaacacac cacacaacag cacaaaccaa aggcagaacc    5100
accacctcaa cacagaccaa caagccgagc acaaaaccac gcctaaaaaa tccaccaaaa    5160
aaaccaaaag atgattacca ttttgaagtg ttcaacttcg ttccctgtag tatatgtggc    5220
aacaatcaac tttgcaaatc catctgtaaa acaataccaa gcaacaaacc aaagaagaaa    5280
ccaaccatca aacccacaaa caaccaacc accaaaacca caaacaaaag acccaaaa     5340 acaccagcca aaacgacgaa aaaagaaact accaccaacc caacaaaaaa accaaccctc    5400
acgaccacag aaagagacac cagcacctca caatccactg tgctcgacac aaccacatta    5460
gaacacacaa tccaacagca atccctccac tcaaccaccc ccgaaaacac acccaactcc    5520
```

```
acacaaacac ccacagcatc cgagccctct acatcaaatt ccacccaaaa tacccaatca   5580
catgcttagt tattcaaaaa ctacatctta gcagaaaacc gtgacctatc aagcaagaac   5640
gaaattaaac ctggggcaaa taaccatgga gctgctgatc cacaggttaa gtgcaatctt   5700
cctaactctt gctattaatg cattgtacct cacctcaagt cagaacataa ctgaggagtt   5760
ttaccaatcg acatgtagtg cagttagcag aggttatttt agtgctttaa gaacaggttg   5820
gtataccagt gtcataacaa tagaattaag taatatataaa gaaaccaaat gcaatggaac   5880
tgacactaaa gtaaaactta taaaacaaga attagataag tataagaatg cagtgacaga   5940
attacagcta cttatgcaaa acacaccagc tgccaacaac cgggccagaa gagaagcacc   6000
acagtatatg aactatacaa tcaataccac taaaaaccta aatgtatcaa taagcaagaa   6060
gaggaaacga agatttctgg gcttcttgtt aggtgtagga tctgcaatag caagtggtat   6120
agctgtatcc aaagttctac accttgaagg agaagtgaac aagatcaaaa atgctttgtt   6180
atctacaaac aaagctgtag tcagtctatc aaatggggtc agtgttttaa ccagcaaagt   6240
gttagatctc aagaattaca taaataacca attattaccc atagtaaatc aacagagctg   6300
tcgcatctcc aacattgaaa cagttataga attccagcag aagaacagca gattgttgga   6360
aatcaacaga gaattcagtg tcaatgcagg tgtaacaaca cctttaagca cttacatgtt   6420
aacaaacagt gagttactat cattgatcaa tgatatgcct ataacaaatg atcagaaaaa   6480
attaatgtca agcaatgttc agatagtaag gcaacaaagt tattctatca tgtctataat   6540
aaaggaagaa gtccttgcat atgttgtaca gctacctatc tatggtgtaa tagatacacc   6600
ttgctggaaa ttacacacat cacctctatg caccaccaac atcaaagaag gatcaaatat   6660
ttgtttaaca aggactgata gaggatggta ttgtgataat gcaggatcag tatccttctt   6720
tccacaggct gacacttgta aagtacagtc caatcgagta ttttgtgaca ctatgaacag   6780
tttgacatta ccaagtgaag tcagcctttg taacactgac atattcaatt ccaagtatga   6840
ctgcaaaatt atgacatcaa aaacagacat aagcagctca gtaattactt ctcttggagc   6900
tatagtgtca tgctatggta aaactaaatg cactgcatcc aacaaaaatc gtgggattat   6960
aaagacattt tctaatggtt gtgactatgt gtcaaacaaa ggagtagata ctgtgtcagt   7020
gggcaacact ttatactatg taaacaagct ggaaggcaag aacctttatg taaaagggga   7080
acctataata aattactatg accctctagt gtttccttct gatgagtttg atgcatcaat   7140
atctcaagtc aatgaaaaaa tcaatcaaag tttagctttt attcgtagat ctgatgaatt   7200
actacataat gtaaatactg gcaaatctac tacaaatatt atgataacta caattattat   7260
agtaatcatt gtagtattgt tatcattaat agctattggt ttgctgttgt attgcaaagc   7320
caaaaacaca ccagttacac taagcaaaga ccaactaagt ggaatcaata atattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgag gcaaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
```

-continued

```
cttcttattg agatcaatag tgatgacatt aaaaagctga gagataatga agaacccaat    7980
tcacctaaga taagagtgta caatactgtt atatcataca ttgagagcaa tagaaaaaac    8040
aacaagcaaa caatccatct gctcaaaaga ctaccagcag acgtgctgaa gaagacaata    8100
aaaaacacat tagatatcca caaaagcata atcataagca acccaaaaga gtcaaccgtg    8160
aatgatcaaa atgaccaaac caaaataat gatattaccg gataaatatc cttgtagtat     8220
atcatccata ttgatttcaa gtgaaagcat gattgctaca ttcaatcata aaaacatatt    8280
acaatttaac cataaccatt tggataacca ccagcgttta ttaaataata tatttgatga    8340
aattcattgg acacctaaaa acttattaga tgccactcaa caatttctcc aacatcttaa    8400
catccctgaa gatatatata caatatatat attagtgtca taatgcttgg ccataacgat    8460
tctatatcat ccaaccataa aactatctta ataaggttat gggacaaaat ggatcccatt    8520
attaatggaa actctgctaa tgtgtatcta actgatagtt atttaaaagg tgttatctct    8580
ttttcagaat gtaatgcttt agggagttac cttttttaacg gcccttatct caaaaatgat    8640
tacaccaact taattagtag acaaagtcca ctactagagc atatgaatct taaaaaacta    8700
actataacac agtcattaat atctagatat cataaaggtg aactgaaatt agaagaacca    8760
acttatttcc agtcattact tatgacatat aaaagcatgt cctcgtctga acaaattgct    8820
acaactaact tacttaaaaa aataatacga agagctatag aaataagtga tgtaaaggtg    8880
tacgccatct tgaataaaact aggactaaag gaaaaggaca gagttaagcc caacaataat    8940
tcaggtgatg aaaactcagt acttacaact ataattaaag atgatatact ttcggctgtg    9000
gaaagcaatc aatcatatac aaattcagac aaaaaatcact cagtaaatca aaatatcact    9060
atcaaaacaa cactcttgaa aaaattgatg tgttcaatgc aacatcctcc atcatggtta    9120
atacactggt tcaatttata tacaaaatta aataacatat taacacaata tcgatcaaat    9180
gaggtaaaaa gtcatgggtt tatattaata gataatcaaa ctttaagtgg ttttcagttt    9240
atttttaaatc aatatggttg tatcgtttat cataaaggac tcaaaaaaat cacaactact    9300
acttacaatc aattttttaac atggaaagac atcagcctta gcagattaaa tgtttgctta    9360
attacttgga taagtaattg tttgaataca ttaaataaaa gcttagggct gagatgtgga    9420
ttcaataatg ttgtgttatc acaattattt ctttatggag attgtatact gaaattattt    9480
cataatgaag gcttctacat aataaaagaa gtagagggat ttattatgtc tttaattcta    9540
aacataacag aagaagatca atttaggaaa cgatttttata atagcatgct aaataacatc    9600
acagatgcag ctattaaggc tcaaaagaac ctactatcaa gggtatgtca cactttatta    9660
gacaagacag tgtctgataa tatcataaat ggtaaatgga taatcctatt aagtaaattt    9720
cttaaattga ttaagcttgc aggtgataat aatctcaata atttgagtga gctatatttt    9780
ctcttcagaa tctttggaca tccaatggtt gatgaaagac aagcaatgga tgctgtaaga    9840
attaactgta atgaaactaa gttctactta ttaagtagtc taagtacgtt aagaggtgct    9900
ttcatttata gaatcataaa agggtttgta aatacctaca acagatggcc cactttaagg    9960
aatgctattg tcctacctct aagatggtta aactattata aacttaatac ttatccatct   10020
ctacttgaaa tcacagaaaa tgatttgatt atttatcag gattgcggtt ctatcgtgaa    10080
tttcatctgc ctaaaaaagt ggatcttgaa atgataataa atgacaaagc catttcacct   10140
ccaaaagatc taatatggac tagttttcct agaaattaca tgccatcaca tatacaaaat   10200
tatatagaac atgaaaagtt gaagttctct gaaagcgaca gatcaagaag agtactagag   10260
```

```
tattacttga gagataataa attcaatgaa tgcgatctat acaattgtgt agtcaatcaa    10320
agctatctca acaactctaa tcacgtggta tcactaactg gtaaagaaag agagctcagt    10380
gtaggtagaa tgtttgctat gcaaccaggt atgtttaggc aaatccaaat cttagcagag    10440
aaaatgatag ccgaaaatat tttacaattc ttccctgaga gtttgacaag atatggtgat    10500
ctagagcttc aaaagatatt agaattaaaa gcaggaataa gcaacaagtc aaatcgttat    10560
aatgataact acaacaatta tatcagtaaa tgttctatca ttacagatct tagcaaattc    10620
aatcaagcat ttagatatga acatcatgt atctgcagtg atgtattaga tgaactgcat    10680
ggagtacaat ctctgttctc ttggttgcat ttaacaatac ctcttgtcac aataatatgt    10740
acatatagac atgcacctcc tttcataaag gatcatgttg ttaatcttaa tgaagttgat    10800
gaacaaagtg gattatacag atatcatatg ggtggtattg agggctggtg tcaaaaactg    10860
tggaccattg aagctatatc attattagat ctaatatctc tcaaagggaa attctctatc    10920
acagctctga taaatggtga taatcagtca attgatataa gtaaaccagt tagacttata    10980
gagggtcaga cccatgctca agcagattat ttgttagcat taaatagcct taaattgcta    11040
tataaagagt atgcaggtat aggccataag cttaagggaa cagagaccta tatcccga    11100
gatatgcagt tcatgagcaa acaatccag cacaatggag tgtactatcc agccagtatc    11160
aaaaagtcc tgagagtagg tccatggata aatacaatac ttgatgattt taagttagt    11220
ttagaatcta taggtagctt aacacaggag ttagaataca gaggggaaag cttattatgc    11280
agtttaatat ttaggaacat ttggttatac aatcaaattg ctttgcaact ccgaaatcat    11340
gcattatgta acaataagct atatttagat atattgaaag tattaaaaca cttaaaaact    11400
ttttttaatc ttgatagtat cgatatggcg ttatcattgt atatgaattt gcctatgctg    11460
tttggtggtg gtgatcctaa tttgttatat cgaagctttt ataggagaac tccagacttc    11520
cttacagaag ctatagtaca ttcagtgttt gtgttgagct attatactgg tcacgattta    11580
caagataagc tccaggatct tccagatgat agactgaaca aattcttgac atgtgtcatc    11640
acattcgata aaaatcccaa tgccgagttt gtaacattga tgagggatcc acaggcgtta    11700
gggtctgaaa ggcaagctaa aattactagt gagattaata gattagcagt aacagaagtc    11760
ttaagtatag ctccaaacaa aatattttct aaaagtgcac aacattatac taccactgag    11820
attgatctaa atgacattat gcaaaatata gaaccaactt accctcatgg attaagagtt    11880
gtttatgaaa gtctaccttt ttataaagca gaaaaaatag ttaatcttat atcaggaaca    11940
aaatccataa ctaatatact tgaaaaaaca tcagcaatag atacaactga tattaatagg    12000
gctactgata tgatgaggaa aaatataact ttacttataa ggatacttcc actagattgt    12060
aacaaagaca aaagagagtt attaagttta gaaaatctta gtataactga attaagcaag    12120
tatgtaagag aaagatcttg gtcattatcc aatatagtag gagtaacatc gccaagtatt    12180
atgttcacaa tggacattaa atatacaact agcactagtc cagtggtat aattatagaa    12240
aaatataatg ttaatagttt aactcgtggt gaaagaggac ctactaagcc atgggtaggt    12300
tcatctacgc aggagaaaaa aacaatgcca gtgtacaata acaagttttt aaccaaaaag    12360
caaagagacc aaatagattt attagcaaaa ttagactggg tatatgcatc catagacaac    12420
aaagatgaat tcatggaaga actgagtact ggaacacttg gactgtcata tgaaaaagcc    12480
aaaaagttgt ttccacaata tctaagtgtc aattatttac accgtttaac agtcagtagt    12540
agaccatgtg aattccctgc atcaatacca gcttatagaa caacaaatta tcatttcgat    12600
actagtccta tcaatcatgt attaacagaa aagtatggag atgaagatat cgacattgtg    12660
```

```
tttcaaaatt gcataagttt tggtcttagc ctgatgtcgg ttgtggaaca attcacaaac    12720
atatgtccta atagaattat tctcataccg aagctgaatg agatacattt gatgaaacct    12780
cctatattta caggagatgt tgatatcatc aagttgaagc aagtgataca aaaacagcat    12840
atgttcctac cagataaaat aagtttaacc caatatgtag aattattcct aagtaacaaa    12900
gcacttaaat ctggatctaa catcaattct aatttaatat tagtacataa aatgtctgat    12960
tattttcata atgcttatat tttaagtact aatttagctg acattggat tctaattatt    13020 caacttatga aagattcaaa aggtattttt gaaaaagatt ggggagaggg gtacataact    13080
gatcatatgt tcattaattt gaatgttttc tttaatgctt ataagactta tttgctatgt    13140
tttcataaag gttatggtaa agcaaaatta gaatgtgata tgaacacttc agatcttctt    13200
tgtgttttgg agttaataga cagtagctac tggaaatcta tgtctaaagt tttcctagaa    13260
caaaaagtca taaatacat agtcaatcaa gacacaagtt tgcatagaat aaaaggctgt    13320
cacagtttta agttgtggtt tttaaaacgc cttaataatg ctaaatttac cgtatgccct    13380
tgggttgtta acatagatta tcacccaaca catatgaaag ctatattatc ttacatagat    13440
ttagttagaa tggggttaat aaatgtagat aaattaacca ttaaaataa aaacaaattc    13500 aatgatgaat tttacacatc aaatctcttt tacattagtt ataacttttc agacaacact    13560
catttgctaa caaaacaaat aagaattgct aattcagaat tagaagataa ttataacaaa    13620
ctatatcacc caaccccaga aactttagaa aatatatcat taattcctgt taaaagtaat    13680
aatagtaaca aacctaaatt ttgtataagt ggaaataccg aatctataat gatgtcaaca    13740
ttctctaata aaatgcatat taaatcttcc actgttacca caagattcaa ttatagcaaa    13800
caagacttgt acaatttatt tccaaatgtt gtgatagaca ggattataga tcattcaggt    13860
aatacagcaa aatctaacca actttacatc accacttcac atcagacatc tttagtaagg    13920
aatagtgcat cactttattg catgcttcct tggcatcatg tcaatagatt aactttgta    13980 tttagttcca caggatgcaa gatcagtata gagtatattt taaaagatct taagattaag    14040
gaccccagtt gtatagcatt cataggtgaa ggagctggta acttattatt acgtacggta    14100
gtagaacttc atccagacat aagatacatt tacagaagtt taaaagattg caatgatcat    14160
agtttaccta ttgaatttct aagattatac aacgggcata taaacataga ttatggtgag    14220
aatttaacca ttcctgctac agatgcaact aataacattc attggtctta tttacatata    14280
aaatttgcag aacctattag catctttgtc tgcgatgctg aattacctgt tacagccaat    14340
tggagtaaaa ttataattga atggagtaag catgtaagaa agtgcaagta ctgttcttct    14400
gtaaatagat gcattttaat cgcaaaatat catgctcaag atgatattga tttcaaatta    14460
gataacatta ctatattaaa aacttacgtg tgcctaggta gcaagttaaa aggatctgaa    14520
gtttacttag tccttacaat aggccctgca aatatacttc ctgttttga tgttgtgcaa    14580 aatgctaaat tgattttttc aagaactaaa aatttcatta tgcctaaaaa aactgacaag    14640
gaatctatcg atgcaaatat taaaagctta ataccttcc tttgttaccc tataacaaaa    14700
aaaggaatta agacttcatt gtcaaaattg aagagtgtag ttaatgggga tatattatca    14760
tattctatag ctggacgtaa tgaagtattc agcaacaagc ttataaacca caagcatatg    14820
aatatcctaa aatggctaga tcatgtttta aattttagat cagctgaact taattacaat    14880
catttataca tgatagagtc cacatatcct tacttaagtg aattgttaaa tagttttaaca    14940 accaatgagc tcaagaaact gattaaaata acaggtagtg tactatacaa ccttcccaac    15000
```

```
-continued gaacagtaac ttaaaatatc attaacaagt ttggtcaaat ttagatgcta acacatcatt    15060
atattatagt tattaaaaaa tatgcaaact tttcaataat ttagcttact gattccaaaa    15120
ttatcatttt atttttaagg ggttgaataa aagtctaaaa ctaacaatga tacatgtgca    15180
tttacaacac aacgagacat tagtttttga cactttttt ctcgt                    15225
```